United States Patent
Sutoris et al.

(12) 
(10) Patent No.: US 6,518,453 B1
(45) Date of Patent: Feb. 11, 2003

(54) METHOD FOR STABILIZING CHEMICAL COMPOUNDS CONTAINING AT LEAST ONE ETHYLENICALLY UNSATURATED BOND IN ORDER TO PREVENT UNDESIRABLE RADICAL POLYMERIZATION

(75) Inventors: Heinz Friedrich Sutoris, Worms (DE); Gerhard Wagenblast, Wachenheim (DE); Volker Schliephake, Schifferstadt (DE); Jürgen Schröder, Ludwigshafen (DE); Klaus Joachim Müller-Engel, Stutensee (DE); Harald Keller, Ludwigshafen (DE); Thomas Jaworek, Kallstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/856,479

(22) PCT Filed: Dec. 7, 1999

(86) PCT No.: PCT/EP99/09543

§ 371 (c)(1), (2), (4) Date: Jul. 3, 2001

(87) PCT Pub. No.: WO00/34220

PCT Pub. Date: Jun. 15, 2000

(30) Foreign Application Priority Data

Dec. 8, 1998 (DE) .......................................... 198 56 565

(51) Int. Cl.⁷ ............................................... C07C 69/52
(52) U.S. Cl. ...................... 560/205; 560/225; 562/598; 526/83; 526/315; 568/448; 568/459; 544/194; 544/195; 585/5; 585/832; 585/435

(58) Field of Search ................................. 560/205, 225; 562/598; 526/315, 83; 568/448, 459; 544/194, 195; 585/5, 832, 435

(56) References Cited

U.S. PATENT DOCUMENTS

| | | | |
|---|---|---|---|
| 3,818,079 A | 6/1974 | Sato et al. | |
| 4,187,382 A | 2/1980 | Cowherd, III et al. | |
| 5,290,888 A | 3/1994 | Gatechair | |
| 5,322,960 A | 6/1994 | Sakamoto et al. | |
| 5,750,765 A | 5/1998 | Nesvadba et al. | |
| 5,919,861 A | 7/1999 | Kazmaier et al. | |
| 6,403,850 B1 | 6/2002 | Benage et al. | |

FOREIGN PATENT DOCUMENTS

| | | |
|---|---|---|
| CN | 1 052 847 | 7/1991 |
| DE | 21 33 921 | 1/1972 |
| DE | 29 13 218 | 10/1980 |
| DE | 197 34 171 | 2/1999 |
| EP | 0 467 850 | 1/1992 |
| EP | 0 685 447 | 12/1995 |
| EP | 0 765 856 | 4/1997 |
| EP | 0 810 196 | 12/1997 |
| WO | WO 98/58891 | 12/1998 |

*Primary Examiner*—Paul J. Killos
(74) *Attorney, Agent, or Firm*—Oblon, Spivak, McClelland, Maier & Neustadt, P.C.

(57) ABSTRACT

In a process for stabilizing chemical compounds having at least one ethylenically unsaturated bond to undesired free radical polymerization, a nitroxyl radical and a chemical compound containing phosphorus in chemically bonded form are added to the unsaturated compound present as pure substance or as a component of a mixture.

11 Claims, No Drawings

METHOD FOR STABILIZING CHEMICAL COMPOUNDS CONTAINING AT LEAST ONE ETHYLENICALLY UNSATURATED BOND IN ORDER TO PREVENT UNDESIRABLE RADICAL POLYMERIZATION

The present invention relates to a process for stabilizing chemical compounds which are present as pure substance or as a component of mixtures and have at least one ethylenically unsaturated group to undesired free radical polymerization, in which polymerization inhibitors which contain:

a) at least one nitroxyl radical (inhibitors a)) and
b) at least one chemical compound containing the element phosphorus in chemically bonded form (inhibitor b))

are added to the pure substance or to the mixture.

Chemical compounds having at least one ethylenically unsaturated group have a pronounced tendency to free radical polymerization owing to their ethylenically unsaturated groups. This is advantageous in that chemical compounds having at least one ethylenically unsaturated group are very suitable for the controlled preparation of polymers by free radical polymerization, as required, for example, for the production of adhesives. At the same time, however, the pronounced tendency to free radical polymerization is disadvantageous in that, both during storage and during the chemical and/or physical processing (e.g. distillation or rectification) of the chemical compounds having at least one ethylenically unsaturated group or mixtures containing them, undesired, spontaneous, free radical polymerization of said chemical compounds can occur, in particular under the action of heat and/or light. Apart from the fact that such uncontrolled free radical polymerizations of the chemical compounds having at least one ethylenically unsaturated group or mixtures containing them constitute a considerable potential danger (free radical polymerizations are highly exothermic and as a consequence frequently explosive), they moreover give rise to a variety of other secondary effects. For example, polymer formed in an undesirable manner during the distillation of mixtures containing chemical compounds having at least one ethylenically unsaturated group may be deposited on the surface of the evaporator (the tendency to polymer formation is higher there owing to the high temperatures) and thus reduce the heat transfer in an undesired manner. However, the polymer formed can also block the baffles in rectification columns, which results in undesired pressure losses. Both require stopping of the rectification process in order to remove the resulting polymer by an expensive procedure.

It is therefore general practice to add both to chemical compounds having at least one ethylenically unsaturated group and to mixtures containing such chemical compounds, both during storage and during the chemical and/or physical processing, compounds which act as inhibitors or retarders of free radical polymerization of the chemical compounds having at least one ethylenically unsaturated group and thus stabilize these chemical compounds to undesired free radical polymerization.

U.S. Pat. No. 5,322,960 discloses the addition of esters of (meth)acrylic acid as polymerization inhibitors to a mixture which contains, inter alia, a nitroxyl radical (a compound which has at least one >N—O.group). An example of a possible nitroxyl radical is, inter alia, 4,4',4''-tris-(2,2,6,6-tetramethylpiperidinooxyl)phosphite, which may also be used as a mixture with other nitroxyl radicals.

EP-A 685 447 likewise recommends the presence of 4,4',4'-tris-(2,2,6,6-tetramethylpiperidinooxyl)phosphite for inhibiting the free radical polymerization of (meth)acrylic acid (in this publication, (meth)acrylic is used as abbreviated notation for "acrylic and/or methacrylic") and/or their esters. Similarly, CN-A 1 052 847 recommends the presence of N-oxyl phosphite esters as free radical polymerization inhibitors. The disadvantage of these polymerization inhibitors containing intramolecularly bonded phosphorus is that the ratio of N-oxyl groups to phosphorus is not variable.

DE-A 21 33 921 relates to a process for preventing the free radical polymerization of α,β-monoethylenically unsaturated carboxylic acids, in which a combination of at least one hydroxyl-containing compound, e.g. cresole, and at least one compound containing the element phosphorus in chemically bonded form, e.g. phosphoric acid or derivatives thereof, is used as a polymerization inhibitor. Phosphoric acid contains the total amount of the phosphorus chemically bonded therein with the oxidation number +5. According to DE-A 21 33 921, the combination of a hydroxyl-containing phenolic compound and a compound containing the element phosphorus in chemically bonded form results in an increased inhibitory effect in a synergistic manner.

DE-A 29 13 218 discloses a process for the preparation of (meth)acrylic esters, in which a mixture of at least one organic ester of phosphorous acid and at least one monohydric or dihydric phenol is added to suppress free radical polymerization.

U.S. Pat. No. 4,187,382 relates to the esterification of organic diols with acrylic acid. It recommends pretreating the diol with triphenyl phosphite in order thus to reduce the tendency of the reaction mixture to undergo free radical polymerization. The use of a conventional phenolic polymerization inhibitor is recommended.

EP-A 810 196 recommends, as polymerization inhibitors for (meth)acrylic acid and its esters, the combination of a nitroxyl radical and a tertiary phosphine in which the phosphorus is covalently bonded to three carbon atoms and has the oxidation number +3. According to EP-A 810 196, the presence of the tertiary phosphine increases the inhibitory effect of nitroxyl radicals in a synergistic manner. The presence of the latter for stabilizing (meth)acrylic esters to undesired free radical polymerization is also recommended in DE-A 19734171.

It is an object of the present invention to provide a process for stabilizing chemical compounds which are present as pure substance or as the component of mixtures and have at least one ethylenically unsaturated group to undesired free radical polymerization, in which polymerization inhibitors which contain at least one nitroxyl radical and at least one further chemical compound which is capable of increasing the inhibitory effect of nitroxyl radicals in a synergistic manner are added to the pure substance or to the mixture.

We have found that this object is achieved by a process for stabilizing chemical compounds which are present as pure substance or as a component of mixtures and have at least one ethylenically unsaturated group to undesired free radical polymerization, in which polymerization inhibitors which contain:

a) at least one nitroxyl radical (inhibitors a)) and
b) at least one chemical compound containing the element phosphorus in chemically bonded form (inhibitor b))
   are added to the pure substance or to the mixture, wherein the at least one inhibitor b) contains on the one hand no N-oxyl group and on the other hand at least a part of the phosphorus chemically bonded with an oxidation number ON of $-3 \leq ON \leq +5$ (frequently $+1 < ON \leq +5$, often $+3 \leq ON \leq +5$), this phosphorus simultaneously being covalently bonded to at least one hetero atom different from carbon.

Initiators b) whose total amount of phosphorus present satisfies the abovementioned definition are preferred.

The oxidation number of an atom within a covalent compound of known structure is intended here to be understood as meaning a number having a positive or negative sign which indicates the charge which the atom would have if the bonding electron pairs of those of the covalent bonds in which it participates are assigned to the electronegative atom in each case within the covalent bond. In the case of electron pairs from covalent bonds between two identical atoms, each atom receives one electron.

In this publication, the electronegativity is a measure of the ability of an atom to attract electrons in a covalent bond as attributable to pauling.

The electronegativities relevant in this publication are those according to H. R. Christen, Grundlagen der allgemeinen und anorganischen Chemie, Verlag Sauerländer, Aarau, Diesterweg.Salle, Frankfurt am Main (1973). For the most important elements of the Periodic Table, these electronegativities have the following values:

Be (1.5); B (2.0); H (2.1); C (2.5); Si (1.8); Ge (1.7); N (3.0); P (2.1); As (2.0); Sb (1.8); O (3.5); S (2.5); Se (2.4); Te (2.1); F (4.0); Cl (3.0); Br (2.8); I (2.4).

Inhibitors b) suitable according to the invention are, for example, those in which the at least one hetero atom different from carbon is hydrogen, nitrogen, oxygen and/or sulfur.

This means that inhibitors b) suitable according to the invention are, for example, the phosphines of the formula $P_nH_{n-2}$ where n=1–7, of the formula $P_nH_n$ where n=3–10, of the formula $P_nH_{n-2}$ where n=4–10 and of the formula $P_nH_{n-4}$ where n=6–9.

Further inhibitors b) according to the invention are the primary and secondary phosphines derived from simplest phosphine, $PH_3$, by (for example partial) substitution of the hydrogen atoms by alkyl and/or aryl, and the quaternary phosphonium bases. Examples are methylphosphine ($CH_3PH_2$), dimethylphosphine (($CH_3$)$_2$PH) and tetramethylphosphoniumhydroxide. The abovementioned alkyl groups expediently have 1 to 10 carbon atoms and the abovementioned aryl groups 6 to 10 carbon atoms. This means that, according to the invention, mono- and diphenyl phosphine are also suitable. Orthophosphoric acids of the formula $H_3PO_n$ (n=2, 3, 4, 5 and 6), the metaphosphoric acids having a lower water content and of the formula $HPO_{n-1}$ (n=3 and 4), the diacids $H_4P_2O_n$ (n=4, 5, 6, 7 and 8) and the polyphosphoric acids having three or more phosphorus atoms per molecule, for example those of the formula $H_{n-2}P_nO_{3n+1}$ (n=3 to 30), and the salts (in particular the alkali metal and ammonium salts) and esters of the abovementioned acids with organic alcohols (in particular $C_1$- to $C_8$-alkanols) are likewise inhibitors b) suitable according to the invention.

Examples are orthophosphoric acid $H_3PO_4$, orthophosphorous acid $H_3PO_3$, hypophosphorous acid $H_3PO_2$ and hypodiphosphoric acid $H_4P_2O_6$.

The above applies to the alkylphosphinic acids, dialkylphosphinic acids and trialkylphosphine oxides formed on careful oxidation of primary, secondary and tertiary alkylphosphines, and to their aryl analogs and the corresponding mixed alkyl/aryl forms. The salts (in particular the alkali metal and ammonium salts) and esters of the alkylphosphinic acids and dialkylphosphinic acids with organic alcohols (in particular $C_1$- to $C_8$-alkanols) are also suitable as inhibitors b).

Examples are methylphosphonic acid, dimethylphosphinic acid and trimethylphosphine oxide:

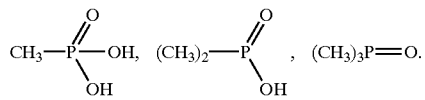

Phosphonous acid $R^*$—P(OH)$_2$, where $R^*$=alkyl (preferably $C_1$- to $C_8$-alkyl) or aryl (preferably phenyl), and phosphinous acid

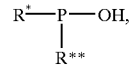

where $R^{**}$, independently of $R^*$ has the same meanings as $R^*$ are also suitable for the novel process.

The same applies to the salts (in particular the alkali metal and ammonium salts) and the esters of these acids with organic alcohols (in particular $C_1$- to $C_8$-alkanols).

Compounds such as pentaphenylphosphorus are likewise suitable inhibitors b) according to the invention.

Derivatives of the oxygen-containing phosphorus compounds described to date, in which one or more O atoms are replaced by S or —NR*, are also inhibitors b) suitable according to the invention. The same applies to compounds consisting only of P and S, such as $P_4S_3$. Furthermore, all phosphorus-containing benzyl phosphonates, phosphites and phosphonites known as plastics stabilizers are suitable as inhibitors b).

The group consisting of the benzyl phosphonates includes, for example, dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate and dioctadecyl-5-tert-butyl-4-hydroxy-3-methylbenzylphosphonate.

The group consisting of the phosphites and phosphonites includes, for example, triphenylphosphite, diphenylalkylphosphite, phenyldialkylphosphite, tris (nonylphenyl)phosphite, trilaurylphosphite, trioctadecylphosphite, distearylpentaerythrityl diphosphite, tris(2,4-di-tert-butylphenyl)phosphite, diisodecyl pentaerythrityl diphosphite, bis(2,4-di-tert-butylphenyl) pentaerythrityl diphosphite, bis(2,6-di-tert-butyl-4-methylphenyl)pentaerythrityl diphosphite, diisodecyloxypentaerythrityl diphosphite, bis(2,4-di-tert-butyl-6-methylphenyl)pentaerythrityl diphosphite, bis(2,4, 6-tris-(tert-butylphenyl))pentaerythrityl diphosphite, tristearyl sorbityl triphosphite, tetrakis(2,4-di-tert-butylphenyl) 4,4'-biphenylene diphosphonite, 6-isooctyloxy-2,4,8,10-tetra-tert-butyl-12H-dibenzo[d,g]-1, 3,2-dioxaphosphocine, 6-fluoro-2,4,8,10-tetra-tert-butyl-12-methyldibenzo[d,g]-1,3,2-dioxaphosphocine, bis(2,4-di-tert-butyl-6-methylphenyl)methyl phosphite and bis(2,4-di-tert-butyl-6-methylphenyl)ethyl phosphite.

According to the invention, preferably used inhibitors b) include orthophosphorous acid and its esters. It is advantageous to use phosphites of the formula (0)

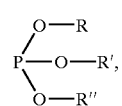

(0)

where R, R', R" may be identical or different and organic radicals, in particular $C_1$–$C_8$-alkyl, hydroxyalkyl of 2 to 4 carbon atoms, haloalkyl, in particular chloroalkyl of 2 to 4 carbon atoms, aryl, in particular phenyl or $C_1$–$C_4$-alkyl-substituted aryl (in particular $C_1$–$C_4$-alkyl-substituted phenyl). Furthermore, two of the three organic radicals R, R' and R", together with the phosphorus and the two oxygen atoms, may form a heterocycle (e.g. 5- or 6-atom).

Specific examples are trimethyl, triethyl, tributyl, trihexyl, trioctyl, triphenyl, tri-p-cresyl, trixylyl, tritolyl and tri-β-chloroethylphosphite. However, dimethyl, diethyl, dibutyl, dioctyl, diphenyl, ditolyl and dixylyl phosphites are also suitable inhibitors b) according to the invention. Inhibitors b) marketed under the trademarks Irgafos® or Ultranox® are, for example

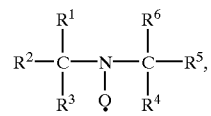

(Irgafos 168)

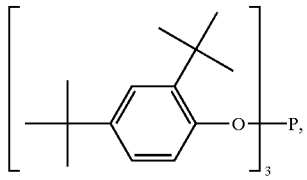

(Iragfos P-EPQ)

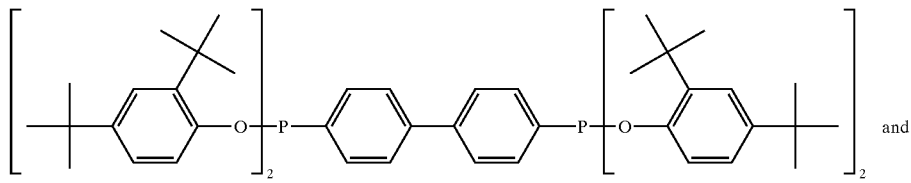
and (Ultranox 626)

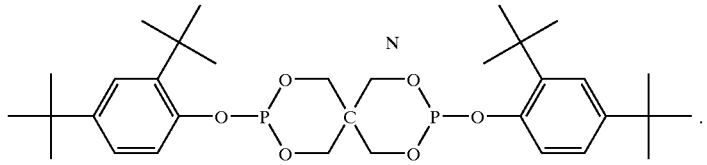

Of course, phosphides too are inhibitors b) which are suitable according to the invention. Mixtures of said inhibitors b) can of course also be used for the novel process.

Nitroxyl radicals (also referred to as N-oxyl radicals) which are suitable according to the invention are in principle all compounds which have at least one >N—O.group. These include all nitroxyl radicals described in DE-A 19734171. The nitroxyl radicals can also be produced in situ from other compounds, for example by H abstraction from hydroxylamines or by an addition reaction of C radicals with nitrones (cf. H. Zweifel in "Stabilization of Polymeric Materials, Springer Verlag, Berlin/Heidelberg (1998), page 52). However, they can also be produced in situ from aromatic amines which are derived from aniline or phenylene diamine (cf. the abovementioned literature page 48). However, all the nitroxyl radicals which are described in the literature cited in DE-A 19734171 are of course also suitable, i.e. nitroxyl radicals suitable according to the invention are in particular those which are derived from a secondary amine which carries no hydrogen atoms on the a-carbon atoms (i.e. the N-oxyl groups are derived from corresponding secondary amino groups). Particularly suitable N-oxyl radicals among these are those which are mentioned in EP-A 135280, the prior application DE-A 19651307, U.S. Pat. Nos. 5,322,912, 5,412,047, 4,581,429, DE-A 1618141, CN-A 1052847, U.S. Pat. Nos. 4,670,131, 5,322,960, the prior application DE-A 19602539, EP-A 765856, WO 98/30601 and JP-A 5/320217.

Such suitable, stable N-oxyl radicals derived from a secondary amine are, for example, those of the formula I $$\begin{array}{c} R^1 \quad\quad R^6 \\ | \quad\quad\quad | \\ R^2-C-N-C-R^5, \\ | \quad\quad\quad | \\ R^3 \quad Q \quad R^4 \end{array}$$ (I)

where
$R^1$, $R^2$, $R^5$ and $R^6$ are identical or different straight-chain or branched, unsubstituted or substituted alkyl and
$R^3$ and $R^4$ are identical or different straight-chain or branched, unsubstituted or substituted alkyl or
$R^3CNCR^4$ is an unsubstituted or substituted, cyclic structure.

Compounds I which are particularly suitable according to the invention are those which are mentioned in EP-A 135 280, the prior application DE-A 19651307, U.S. Pat. Nos. 5,322,912, 5,412,047, 4,581,429, DE-A 16 18 141, CN-A 1052847, U.S. Pat. Nos. 4,670,131, 5,322,960 and the prior application DE-A 19602539.

Examples of these are those stable N-oxyl radicals of the formula I in which $R^1$, $R^2$, $R^5$ and $R^6$ are (identical or different) $C_1$- to $C_4$-alkyl groups such as methyl, ethyl, n-propyl, iso-propyl, n-butyl, iso-butyl or tert-butyl, linear or branched pentyl, phenyl or substituted groups thereof and $R^3$ and $R^4$ are (identical or different) $C_1$- to $C_4$-alkyl groups such as methyl, ethyl, n-propyl, iso-propyl, n-butyl, iso-butyl or tert-butyl, linear or branched pentyl, substituted groups thereof or, together with CNC, the cyclic structure

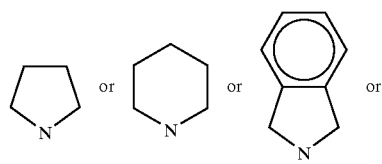

-continued

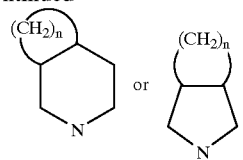

where n is an integer from 1 to 10 (in particular 1 to 6), including substituted cyclic structures of these types. Typical examples are 2,2,6,6-tetramethyl-1-oxyl-piperidine, 2,2,5,5-tetramethyl-1-oxyl-pyrrolidine and 4-oxo-2,2,6,6-tetramethyl-1-oxyl-piperidine.

The N-oxyl radicals I can be prepared from the corresponding secondary amines by oxidation, for example with hydrogen peroxide. As a rule, they can be prepared as pure substance.

The N-oxyl radicals I suitable according to the invention include in particular piperidine or pyrrolidine-N-oxyls and di-N-oxyls of the formulae II to IX below:

(II)
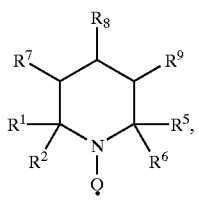

(III)
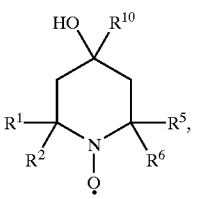

(IV)
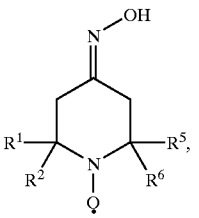

(V)
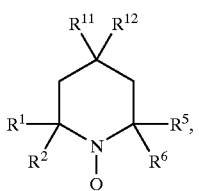

(VI)
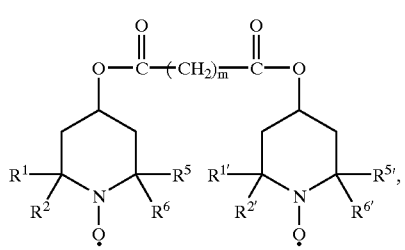

(VII)
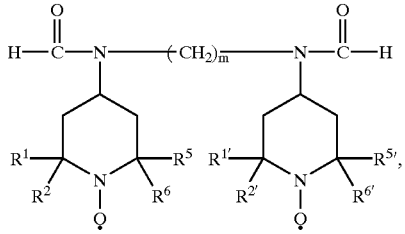

(VIII)
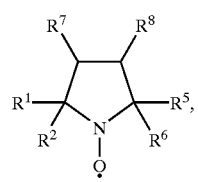

(IX)
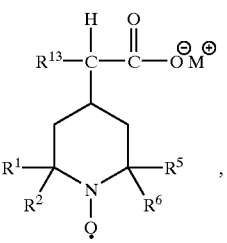

where
m is from 2 to 10,
$R^7$, $R^8$, $R^9$ independently of one another, are each

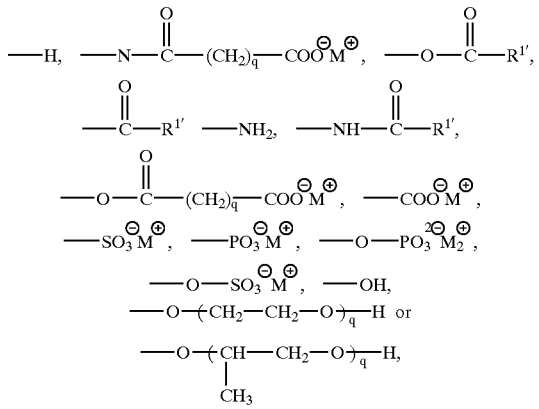

$M^{\oplus}$, is a hydrogen ion or an alkali metal ion,
q is an integer from 1 to 10,
$R^{1'}$, $R^{2'}$, $R^{5'}$, $R^{6'}$ independently of one another and independently of $R^1$, $R^2$, $R^5$, $R^6$ are each the same groups as $R^1$,
$R^{10}$ is $C_1$- to $C_4$-alkyl, —CH=CH$_2$, —C≡CH, —CN,

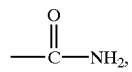

—COO$^{\ominus}$ M$^{\oplus}$, —COOCH$_3$ or —COOC$_2$H$_5$,
$R^{11}$ is an organic radical which has at least one primary, secondary (e.g. —NHR$^1$) or tertiary amino group (e.g. —NR$^1$R$^2$) or at least one ammonium group —N$^{\oplus}$, $R^{14}R^{15}R^{16}X^{\ominus}$, where $X^{\ominus}$ =F$^{\ominus}$, Cl$^{\ominus}$, Br$^{\ominus}$, $HSO_4^\ominus$, $SO_4^{2\ominus}$, $H_2PO_4^\ominus$, $HPO_4^{2\ominus}$, or $PO_4^{3\ominus}$ and $R^{14}$, $R^{15}$, $R^{16}$, independently of one another, are organic radicals (e.g. independently of one another and independently of $R^1$, the same groups as $R^1$), $R^{12}$ independently of $R^{11}$, is the same groups as $R^{11}$ or —H, —OH, $C_1$- to $C_4$-alkyl, —COO$^\ominus$ M$^\oplus$, —C≡CH,

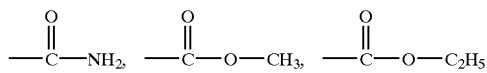

or hydroxyl-substituted $C_1$- to $C_4$-alkyl (e.g. hydroxyethyl or hydroxypropyl) or $R^{11}$, $R^{12}$ together are the oxygen of a carbonyl group and $R^{13}$ is —H, —CH$_3$ or

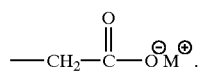

Preferably, $R^1=R^2=R^5=R^6=R^{1'}=R^{2'}=R^{5'}=R^{6'}$=—CH$_3$.

Typical examples of N-oxyl radicals suitable according to the invention are 1-oxyl-2,2,6,6-tetramethylpiperidine, 1-oxyl-2,2,6,6-tetramethylpiperidin-4-ol, 1-oxyl-2,2,6,6-tetramethyl-4-methoxypiperidine, 1-oxyl-2,2,6,6-tetramethyl-4-ethoxypiperidine, 1-oxyl-2,2,6,6-tetramethyl-4-trimethylsiloxypiperidine, 1-oxyl-2,2,6,6-tetramethylpiperidin-4-one, 1-oxyl-2,2,6,6-tetramethylpiperidin-4-yl acetate, 1-oxyl-2,2,6,6-tetramethylpiperidin-4-yl 2-ethylhexanoate, 1-oxyl-2,2,6,6-tetramethylpiperidin-4-yl stearate, 1-oxyl-2,2,6,6-tetramethylpiperidin-4-yl benzoate, 1-oxyl-2,2,6,6-tetramethylpiperidin-4-yl 4-tert-butylbenzoate, bis(1-oxyl-2,2,6,6-tetramethylpiperidin-4-yl)succinate, bis(1-oxyl-2,2,6,6-tetramethylpiperidin-4-yl)adipate, bis(1-oxyl-2,2,6,6-tetramethylpiperidin-4-yl)sebacate, bis(1-oxyl-2,2,6,6-tetramethylpiperidin-4-yl)n-butylmalonate, bis(1-oxyl-2,2,6,6-tetramethylpiperidin-4-yl)phthalate, bis(-oxyl-2,2,6,6-tetramethylpiperidin-4-yl)isophthalate, bis(1-oxyl-2,2,6,6-tetramethylpiperidin-4-yl)terephthalate, bis(1-oxyl-2,2,6,6-tetramethylpiperidin-4-yl)hexahydroterephthalate, N,N'-bis(1-oxyl-2,2,6,6-tetramethylpiperidin-4-yl)adipamide, N-(1-oxyl-2,2,6,6-tetramethylpiperidin-4-yl)caprolactam, N-(1-oxyl-2,2,6,6-tetramethylpiperidin-4-yl)dodecylsuccinimide, 2,4,6-tris-[N-butyl-N-(1-oxyl-2,2,6,6-tetramethylpiperidin-4-yl)]s-triazine, N,N'-bis(1-oxyl-2,2,6,6-tetramethylpiperidin-4-yl) N,N'-bis-formyl-1,6-diaminohexane, 4,4'-ethylenebis(1-oxyl-2,2,6,6-tetramethylpiperazin-3-one) and tris(2,2,6,6-tetramethyl-1-oxyl-piperidin-4-yl)phosphite and additionally 1-oxyl-2,2,6,6-tetramethyl-1,2,3,6-tetrahydropyridine.

The compounds (VI) and (VII) can be obtained according to U.S. Pat. No. 4,665,185 (e.g. Example 7) and DE-A 19510184.

Further suitable typical examples are:

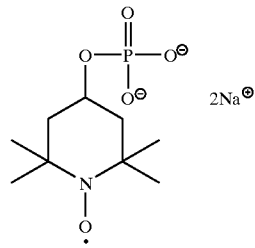

Sunamoto, Junzo; Akiyoshi, Kuzunari, Kihara, Tetsuji; Endo, Masayuki, BCS JA 8, Bull. Chem. Soc. Jpn., En, 65, 4, (1992), 1041–1046;

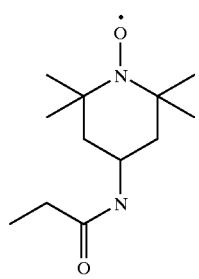

Beilstein Registry Number 6926369 ($C_{11}H_{22}N_3O_2$);

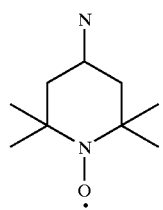

Beilstein Registry Number 6498805 (4-amino-2,2,6,6-tetramethyl-1-oxyl-piperidine);

-continued

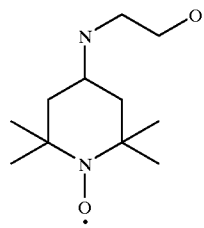

Beilstein Registry Number 6800244 ($C_{11}H_{23}N_2O_2$);

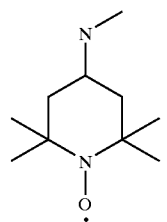

Beilstein Registry Number 5730772 (N-methyl-4-amino-2,2,6,6-tetra-methyl-1-oxylpiperidine;

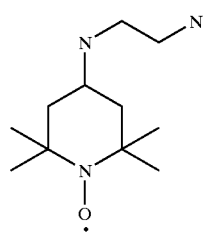

Beilstein Registry Number 5507538 (2,2,6,6-tetramethyl-4-(2-amino-ethylamino)-1-oxylpiperidine);

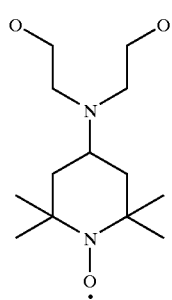

Beilstein Registry Number 4417950 (4<Bis(2-hydroxyethyl)>-amino-2,2,6,6-tetramethyl-1-oxyl-piperidine);

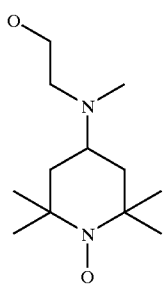

Beilstein Registry Number 4396625 ($C_{12}H_{25}N_2O_2$);

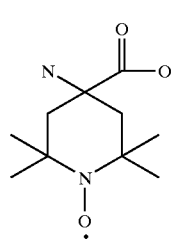

Beilstein Registry Number 4139900 (4-amino-2,2,6,6-tetra-methyl-4-carboxyl-1-oxylpiperidine);

-continued

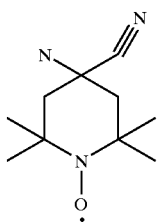
Beilstein Registry Number 4137088 (4-amino-4-cyano-2,2,6,6-tetra-methyl-1-oxylpiperidine);

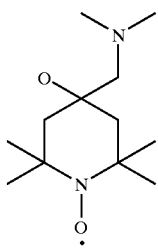
Beilstein Registry Number 3942714 ($C_{12}H_{25}N_2O_2$);

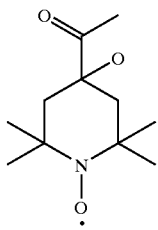
Beilstein Registry Number 1468515 (2,2,6,6-tetramethyl-4-hydroxy-4-acetyl-1-oxylpiperidine);

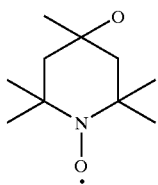
Beilstein Registry Number 1423410 (2,2,4,6,6-pentamethyl-4-hydroxy-1-oxylpiperidine);

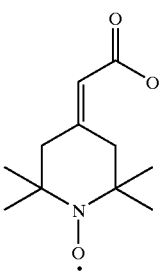
Beilstein Registry Number 6205316 (4-carboxymethylen-2,2,6,6-tetra-methyl-1-oxylpiperidine);

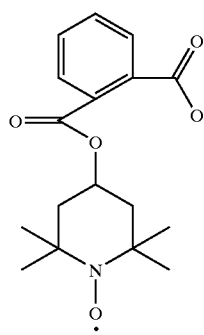
Beilstein Registry Number 1395538 (4-<2-carboxy-benzoyloxy>-2,2,6,6-tetramethyl-1-oxylpiperidine);

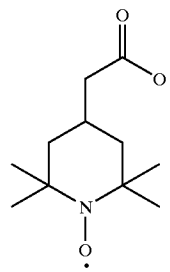
Beilstein Registry Number 3546230 (4-carboxymethyl-2,2,6,6-tetramethyl-1-oxylpiperidine);
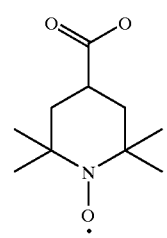
Beilstein Registry Number 3949026 (4-carboxyl-2,2,6,6-tetramethyl-1-oxylpiperidine);
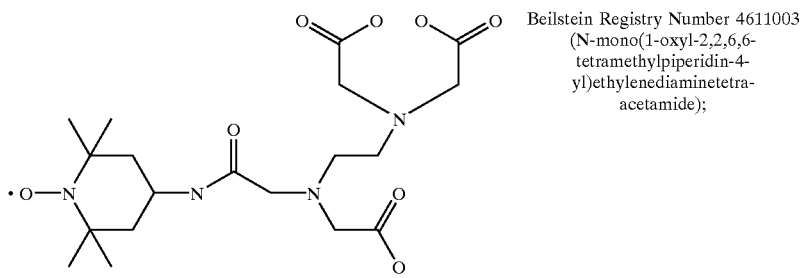
Beilstein Registry Number 4611003 (N-mono(1-oxyl-2,2,6,6-tetramethylpiperidin-4-yl)ethylenediaminetetraacetamide);
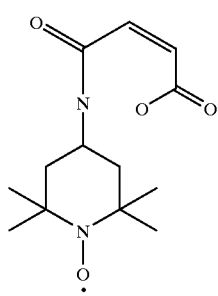
Beilstein Registry Number 5961636 ($C_{13}H_{21}N_2O_4$)
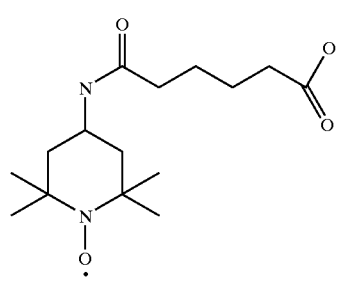
Beilstein Registry Number 5592232 ($C_{15}H_{27}N_2O_4$);

-continued

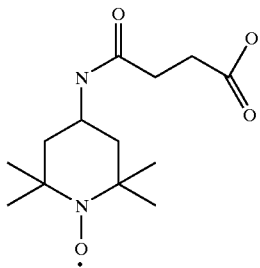
Beilstein Registry Number 5080576 (N-mono-2,2,6,6-tetramethyl-1-oxyl-4-piperidinyl)succinamide);

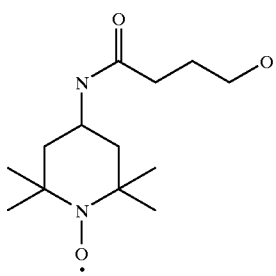
Beilstein Registry Number 5051814 (4-(4-hydroxybutanoylamino)-2,2,6,6-tetramethyl-1-oxyl-piperidine);

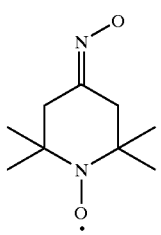
Beilstein Registry Number 4677496 (2,2,6,6-tetramethyl-4-oximino-1-oxylpiperidine);

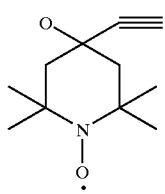
Beilstein Registry Number 1451068 ($C_{11}H_{18}NO_2$);

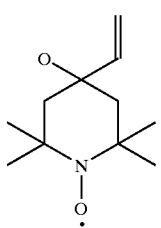
Beilstein Registry Number 1451075 ($C_{11}H_{20}NO_2$);

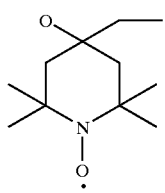
Beilstein Registry Number 1423698 (4-ethyl-4-hydroxy-2,2,6,6-tetramethyl-1-oxylpiperidine);

-continued

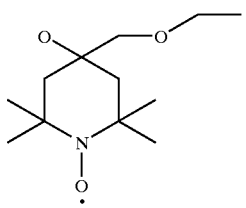
Beilstein Registry Number 5509793
(4-ethoxymethyl-4-hydroxy-2,2,6,6-tetramethyl-1-oxylpiperidine);

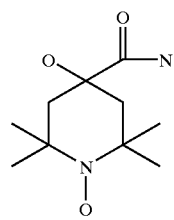
Beilstein Registry Number 3960373
($C_{10}H_{19}N_2O_3$);

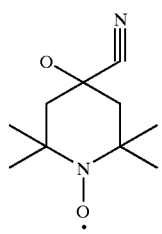
Beilstein Registry Number
($C_{10}H_{17}N_2O_2$);

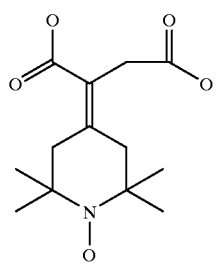
Beilstein Registry Number 3985130
(2,2,6,6-tetramethyl-1-oxyl-4-piperidylidene)succinic acid.

Further N-oxyl radicals suitable according to the invention are those which are disclosed in WO 98/44008, WO 97/46593 and DE-A 19743396.

According to the invention, mixtures of N-oxyl radicals can of course also be used.

In the novel process, as a rule from 1 to 1000, frequently from 50 to 500, ppm by weight (based on the amount contained of the at least one chemical compound having at least one ethylenically unsaturated group) of at least one inhibitor a) is added to the chemical compound present as pure substance or as a component of mixtures and having at least one ethylenically unsaturated group.

The molar ratio of inhibitors a) to be added according to the invention to inhibitors b) to be added according to the invention is usually from 1:100 to 100:1, frequently from 10:90 to 10:10.

Of course, the inhibitor system to be added in the novel process may also comprise further components inhibiting free radical polymerization, in addition to inhibitors a) and inhibitors b).

Examples of such other free radical polymerization inhibitors are organic nitroso compounds, such as N-nitrosoarylamines or nitroso compounds having the nitroso group bonded directly to a carbon atom of an aromatic nucleus.

Examples are nitrosophenols, such as 4-nitrosophenol, as well as nitrosobenzene. Further examples of other polymerization inhibitors are the p-phenylenediamines stated in DE-A 19734171, phenolic compounds, such as hydroquinone or its methyl ether or compounds such as phenothiazine.

It is advantageous that the inhibitor mixture to be used according to the invention also displays its activity in the presence of molecular oxygen.

Suitable chemical compounds having at least one monoethylenically unsaturated group and to which the novel process can be applied include compounds such as olefins, e.g. isobutene, ethylene and propylene, vinylaromatic monomers, such as styrene, α-methylstyrene, o-chlorostyrene or vinyltoluenes, conjugated $C_4$–$C_8$ dienes, such as butadiene or isoprene, and esters of vinyl alcohol and monocarboxylic acids of 1 to 18 carbon atoms, such as vinyl acetate, vinyl propionate, vinyl n-butyrate, vinyl laurate and vinyl stearate.

However, the novel process is particularly suitable in the case of α,β-monoethylenically unsaturated mono- and dicarboxylic acids of 3 to 6 carbon atoms, in particular acrylic acid, methacrylic acid, maleic acid, fumaric acid and itaconic acid, the esters of the abovementioned carboxylic acids and alkanols of 1 to 12, often 1 to 8, frequently 1 to 4, carbon atoms, in particular methyl, ethyl, n-butyl, isobutyl tert-butyl and 2-ethylhexyl acrylate and methacrylate, dimethyl maleate or di-n-butyl maleate. However, the novel process is also suitable in the case of the precursor aldehydes, nitriles and amides of the abovementioned α,β-monoethylenically unsaturated mono- and dicarboxylic acids of 3 to 6 carbon atoms, e.g. acrolein, methacrolein, acrylonitrile, methacrylonitrile, acrylamide and methacrylamide. It can however also be used in the case of monomers such as vinylsulfonic acid and N-vinylpyrrolidone.

The novel process is suitable for stabilizing compounds having at least one monoethylenically unsaturated group both during storage and in the process (preparation and purification (e.g. distillation) and chemical reaction). The latter also applies to distillative treatments at from 50 to 300° C., frequently from 50 to 200° C. or alternatively from 50 to 150° C.

The novel process is particularly suitable for stabilization in the distillative (rectificative) treatment of (meth)acrylates (in particular of the abovementioned typical examples) and in their distillative or rectificative separation from product mixtures, such as those which result from a (homogeneously and/or heterogeneously) acid-catalyzed esterification of (meth)acrylic acid with alcohols, in particular alkanols (especially $C_1$- to $C_{12}$- or $C_1$- to $C_8$-alkanols) before and/or after removal of the acid catalyst.

However, it is also suitable for stabilizing mixtures which contain the abovementioned (meth)acrylate and which contain neither the acidic esterification catalyst nor acrylic acid or methacrylic acid. Such mixtures containing (meth) acrylates form, for example, the abovementioned esterification product mixtures after, for example, extractive (for example by means of water and/or aqueous alkali) and/or rectificative removal of the acid catalyst and after corresponding removal of the excess (meth)acrylic acid.

Stabilization of a (meth)acrylate-containing mixture subjected to a distillation (rectification) can be effected in a simple manner by adding the inhibitors to be added according to the invention to the mixture before distillation (rectification). The addition can also be effected in the feed to the distillation (rectification). In both the abovementioned cases, it may be expedient also to add inhibitor at the top of the column to stabilize the column. Of course, the overall stabilization can also be carried out exclusively by adding inhibitor at the top of the column.

In the novel process, it is of course possible to add the inhibitors a) and inhibitors b) in succession, simultaneously or in premixed form. The abovementioned also applies to the other inhibitors if the inhibitor mixture comprises such inhibitors. Of course, in the case of the abovementioned application of the novel process, molecular oxygen or a mixture thereof with an inert gas, e.g. air, may flow through the distillation (rectification) columns.

Furthermore, the addition of inhibitors a) and inhibitors b) can also be effected at different locations. For example, the inhibitors b) can be added at the top of the rectification column and the inhibitors a) to the bottom and/or to the feed of the rectification column. This applies both for those rectifications in the course of which the (meth)acrylate is removed via a top take-off, via a bottom take-off and/or via a side take-off. It may also be expedient in the case of a continuous distillative (rectificative) separation of (meth) acrylates to carry out the novel process so that the at least one inhibitor b) to be added according to the invention is introduced not continuously but only from time to time, i.e. periodically (e.g. at the top of the column, at the bottom and/or in the feed).

All statements made about the novel stabilization in the distillative (rectificative) separation of (meth)acrylates from acid-catalyzed esterification mixtures applies in the same way also in respect of a distillative (rectificative) separation of (meth)acrylic acid or (meth)acrolein from mixtures containing them.

(Meth)acrylic acid is obtainable, inter alia, by a catalytic gas-phase oxidation of alkanes, alkanols, alkenes or alkenals which contain 3 or 4 carbon atoms. (Meth)acrylic acid is particularly advantageously obtainable, for example, by catalytic gas-phase oxidation of propane, propene, tert-butanol, isobutene, isobutane, isobutyraldehyde or methacrolein. However, other possible starting compounds are those from which the actual $C_3$-/$C_4$ starting compound forms initially as an intermediate during the gas-phase oxidation. An example is the methyl ether of tert-butanol.

These starting gases, as a rule diluted with inert gases, such as nitrogen, CO, $CO_2$, saturated hydrocarbons and/or steam, are passed, in the form of a mixture with oxygen at elevated temperatures (usually from 200 to 400° C.) and, if required, superatmospheric pressure, over transition metal (e.g. Mo, V, W and/or Fe-containing) mixed oxide catalysts and oxidized to (meth)acrylic acid (cf. for example DE-A 4 405 059, EP-A 253 409, EP-A 92 097, DE-A 44 31 957, DE-A 44 31 949, CN-A 11 053 52 and WO 97/36849).

Owing to the numerous parallel and subsequent reactions taking place in the course of the catalytic gas-phase oxidation and owing to the inert diluent gases present, however, the catalytic gas-phase oxidation gives, instead of pure (meth)acrylic acid, a reaction gas mixture which essentially contains (meth)acrylic acid, the inert diluent gases and by-products, from which the (meth)acrylic acid has to be separated off. In addition to by-products, e.g. acetic acid, which are comparatively simple to remove from (meth) acrylic acid and cause fewer problems in subsequent applications of the (meth)acrylic acid, the reaction gas mixture frequently also contains lower aldehydes which are closely related to (meth)acrylic acid and therefore difficult to separate from (meth)acrylic acid, e.g. formaldehyde, acetaldehyde, acrolein, methacrolein, propionaldehyde, n-butyraldehyde, benzaldehyde, furfural and crotonaldehyde, and may additionally contain maleic anhydride (the total amount of these by-products which frequently cause considerable problems in subsequent applications is as a rule $\leq 2$, in general $\geq 0.05$, % by weight, based on the amount of (meth)acrylic acid contained in the reaction gas mixture).

DE-A 44 36 243 relates to a process for separating (meth)acrylic acid from the reaction gas mixture of the catalytic gas-phase oxidation by countercurrent absorption with a high-boiling inert hydrophobic organic liquid, in which the reaction gas mixture is fed, in an absorption column, countercurrent to the descending high-boiling inert hydrophobic organic liquid, a rectification process is superposed on the absorption process taking place in a natural manner in the absorption column, by withdrawing from the absorption column an amount of energy over and above its natural energy release taking place as a result of its contact with ambient temperature, and the (meth)acrylic acid is separated by rectification from the liquid discharge of the absorption column (absorbate), which liquid discharge contains (meth)acrylic acid and the absorbent as main components and lower aldehydes and possible maleic anhydride as secondary components. The (meth)acrylic acid obtainable is referred to as crude (meth)acrylic acid. As a rule, it has a purity of >98% by weight.

As high-boiling inert hydrophobic organic liquid (absorbent), DE-A 44 36 243 includes all those liquids whose boiling point at atmospheric pressure (1 atm) is above the boiling point of (meth)acrylic acid and at least 70% by weight of which comprises those molecules which contain no externally acting polar group and thus, for example, are not capable of forming hydrogen bridges. These definitions are also applicable here. DE—C 2 136 396 and DE-A 43 08 087 likewise disclose separation of acrylic acid from the reaction gas mixture of the catalytic gas-phase oxidation of propylene and/or acrolein by countercurrent absorption with a high-boiling inert hydrophobic organic liquid. The process is essentially carried out by feeding the reaction gas mixture countercurrent to the descending absorption liquid in a conventional absorption column, then, in a desorption column, by substantially removing the readily volatile secondary components, which can be easily separated off, from the liquid discharge of the absorption column, which is essentially composed of acrylic acid, the absorbent and secondary components by stripping with inert gas and subjecting the liquid discharge of the desorption column, containing (meth)acrylic acid and the absorbent as main components, to rectificative treatment to separate off crude acrylic acid.

DE-A 2 235 326 likewise relates to the problem of the rectificative isolation of (meth)acrylic acid from a mixture thereof with organic solvents having a higher boiling point than (meth)acrylic acid, this prior art also mentioning in particular higher alcohols or esters of these or other alcohols, in particular with (meth)acrylic acid, as organic solvents to be considered.

DE-A 19810962 likewise relates to the problem of the rectificative isolation of (meth)acrylic acid from mixtures thereof with organic solvents having a higher boiling point than (meth)acrylic acid.

However, the problem of rectificative isolation of (meth) acrylic acid also arises when the (meth)acrylic acid from the reaction gases of the catalytic gas-phase oxidation is first taken up in water and the water is then removed from the aqueous (meth)acrylic acid-containing mixtures by rectification with the addition of an organic azeotropic entraining agent.

However, it is also present in the rectificative preparation of pure acrylic acid (purity>99.7% by weight) from crude acrylic acid (purity>99% by weight).

In the case of all these abovementioned rectification problems, the novel method of inhibition can be used analogously to the described isolation of (meth)acrylate by rectification. If the high-boiling hydrophobic organic solvent with which the (meth)acrylic acid is extracted from the reaction mixture of the gas-phase oxidation is recycled, i.e. circulated, for extraction after the isolation of (meth)acrylic acid by rectification, it may be expedient from time to time to add inhibitors b) to the high-boiling hydrophobic organic solvent separated off, before it is reused for the extraction. Of course, the novel process can also be used in the extraction of the (meth)acrylic acid from the reaction mixture of the gas-phase oxidation itself. The novel stabilization is also advisable for the separation of mixtures containing (meth)acrylic acid or esters thereof by crystallization.

In other words, the novel inhibition process can be used in principle for all separation problems discussed in DE-A 19851983, DE-A 19851984, DE-A 19838783, DE-A 19838817, DEA 19838845, DE-A 19836307, DE-A 1983795, DE-A 19837519, DE-A 19837520, DE-A 19837517, DE-A 19837518, DEA 19832962 and DE-A 19833049 and relating to (meth)acrylic acid and/or esters thereof.

As stated above, it can also be used for a distillative (rectificative) separation of (meth)acrolein from mixtures containing the latter. (Meth)acrolein is obtainable in a similar manner to (meth)acrylic acid, for example by catalytic gas-phase oxidation. However, the oxidation is no t continued after the first oxidation stage. Rather, the (meth)acrolein contained in the reaction gas mixture is as a rule first separated from the reaction gas mixture by extraction with water and then obtained from the aqueous solution by distillation (rectification). The novel stabilization process is suitable for all process steps stated.

It is surprising according to the invention that inhibitors a) and b) have pronounced synergistic activity with respect to the stabilization of chemical compounds which a re present as pure substance or as a component of mixtures and have at least one ethylenically unsaturated group to undesired free radical polymerization. This applies essentially independently of the pH and both for lower (e.g. room temperature) and for elevated temperatures, as are usual, for example, in thermal physical separation processes as well as the chemical reactions taking place at elevated temperatures.

The abovementioned is applicable in particular to the stabilization of (meth)acrylic acid and/or esters thereof whose ethylenically unsaturated double bond is particularly active with respect to free radical polymerization.

According to the invention, the inhibitors a) and b) are as a rule chosen so that they are completely soluble in the amount in which they are used in the substance to be stabilized. They are frequently added not as pure substance but as suspension, emulsion or solution. Particularly suitable solvents and/or dispersing media are those substances which are part of the system to be stabilized, i.e., for example, in the case of chemical reactions, such as esterifications, all starting materials and products and, in the case of extractions, in particular the extraction medium or a component thereof. Combinations of inhibitors a) and inhibitors b) which are particularly suitable according to the invention are:

| Inhibitor a) | Inhibitor b) |
| --- | --- |
| 4-Hydroxy-2,2,6,6-tetra-methyl-1-oxylpiperidine | $P(OH)_3$ |
| 4-Hydroxy-2,2,6,6-tetra-methyl-1-oxylpiperidine | $P(OMethyl)_3$ |
| 4-Hydroxy-2,2,6,6-tetra-methyl-1-oxylpiperidine | $P(OEthyl)_3$ |
| 4-Hydroxy-2,2,6,6-tetra-methyl-1-oxylpiperidine | $P(Oiso\text{-}Propyl)_3$ |
| 4-Hydroxy-2,2,6,6-tetra-methyl-1-oxylpiperidine | $P(OPropyl)_3$ |
| 4-Hydroxy-2,2,6,6-tetra-methyl-1-oxylpiperidine | $P(On\text{-}Butyl)_3$ |
| 4-Hydroxy-2,2,6,6-tetra-methyl-1-oxylpiperidine | $P(Osec\text{-}Butyl)_3$ |
| 4-Hydroxy-2,2,6,6-tetra-methyl-1-oxylpiperidine | $P(Otert.\text{-}Butyl)_3$ |
| 4-Hydroxy-2,2,6,6-tetra-methyl-1-oxylpiperidine | $P(OPhenyl)_3$ |
| 4-Hydroxy-2,2,6,6-tetra-methyl-1-oxylpiperidine | $P(OH)(OMethyl)_2$ |
| 4-Hydroxy-2,2,6,6-tetra-methyl-1-oxylpiperidine | $P(OH)(OEthyl)_2$ |
| 4-Hydroxy-2,2,6,6-tetra-methyl-1-oxylpiperidine | $P(OH)(Oiso\text{-}Propyl)_2$ |
| 4-Hydroxy-2,2,6,6-tetra-methyl-1-oxylpiperidine | $P(OH)(OPropyl)_2$ |
| 4-Hydroxy-2,2,6,6-tetra-methyl-1-oxylpiperidine | $P(OH)(On\text{-}Butyl)_2$ |
| 4-Hydroxy-2,2,6,6-tetra-methyl-1-oxylpiperidine | $P(OH)(Osec\text{-}Butyl)_2$ |
| 4-Hydroxy-2,2,6,6-tetra-methyl-1-oxylpiperidine | $P(OH)(Otert.\text{-}Butyl)_2$ |

-continued

| Inhibitor a) | Inhibitor b) |
|---|---|
| 4-Hydroxy-2,2,6,6-tetramethyl-1-oxylpiperidine | $P(OH)(OPhenyl)_2$ |
| 4-Hydroxy-2,2,6,6-tetramethyl-1-oxylpiperidine | $P(OH)_2(OMethyl)$ |
| 4-Hydroxy-2,2,6,6-tetramethyl-1-oxylpiperidine | $P(OH)_2(OEthyl)$ |
| 4-Hydroxy-2,2,6,6-tetramethyl-1-oxylpiperidine | $P(OH)_2(Oiso\text{-Propyl})$ |
| 4-Hydroxy-2,2,6,6-tetramethyl-1-oxylpiperidine | $P(OH)_2(OPropyl)$ |
| 4-Hydroxy-2,2,6,6-tetramethyl-1-oxylpiperidine | $P(OH)_2(On\text{-Butyl})$ |
| 4-Hydroxy-2,2,6,6-tetramethyl-1-oxylpiperidine | $P(OH)_2(Osec\text{-Butyl})$ |
| 4-Hydroxy-2,2,6,6-tetramethyl-1-oxylpiperidine | $P(OH)_2(Otert.\text{-Butyl})$ |
| 4-Hydroxy-2,2,6,6-tetramethyl-1-oxylpiperidine | $P(OH)_2(OPhenyl)$ |
| 4-Hydroxy-2,2,6,6-tetramethyl-1-oxylpiperidine | $HP(OH)_2$ |
| 4-Hydroxy-2,2,6,6-tetramethyl-1-oxylpiperidine | $(Methyl)P(OMethyl)_2$ |
| 4-Hydroxy-2,2,6,6-tetramethyl-1-oxylpiperidine | $(Ethyl)P(OEthyl)_2$ |
| 4-Hydroxy-2,2,6,6-tetramethyl-1-oxylpiperidine | $(iso\text{-Propyl})P(Oiso\text{-Propyl})_2$ |
| 4-Hydroxy-2,2,6,6-tetramethyl-1-oxylpiperidine | $(Propyl)P(OPropyl)_2$ |
| 4-Hydroxy-2,2,6,6-tetramethyl-1-oxylpiperidine | $(n\text{-Butyl})P(On\text{-Butyl})_2$ |
| 4-Hydroxy-2,2,6,6-tetramethyl-1-oxylpiperidine | $(sec\text{-Butyl})P(Osec\text{-Butyl})_2$ |
| 4-Hydroxy-2,2,6,6-tetramethyl-1-oxylpiperidine | $(tert.\text{-Butyl})P(Otert.\text{-Butyl})_2$ |
| 4-Hydroxy-2,2,6,6-tetramethyl-1-oxylpiperidine | $(Phenyl)P(OPhenyl)_2$ |
| 4-Hydroxy-2,2,6,6-tetramethyl-1-oxylpiperidine | $O=P(OH)_3$ |
| 4-Hydroxy-2,2,6,6-tetramethyl-1-oxylpiperidine | $O=P(OMethyl)_3$ |
| 4-Hydroxy-2,2,6,6-tetramethyl-1-oxylpiperidine | $O=P(OEthyl)_3$ |
| 4-Hydroxy-2,2,6,6-tetramethyl-1-oxylpiperidine | $O=P(OPropyl)_3$ |
| 4-Hydroxy-2,2,6,6-tetramethyl-1-oxylpiperidine | $O=P(Oiso\text{-Propyl})_3$ |
| 4-Hydroxy-2,2,6,6-tetramethyl-1-oxylpiperidine | $O=P(On\text{-Butyl})_3$ |
| 4-Hydroxy-2,2,6,6-tetramethyl-1-oxylpiperidine | $O=P(Osec\text{-Butyl})_3$ |
| 4-Hydroxy-2,2,6,6-tetramethyl-1-oxylpiperidine | $O=P(Otert.\text{-Butyl})_3$ |
| 4-Hydroxy-2,2,6,6-tetramethyl-1-oxylpiperidine | $O=P(OPhenyl)_3$ |
| 4-Hydroxy-2,2,6,6-tetramethyl-1-oxylpiperidine | $HO-\overset{O}{\underset{\|}{P}}(OMethyl)_2$ |
| 4-Hydroxy-2,2,6,6-tetramethyl-1-oxylpiperidine | $HO-\overset{O}{\underset{\|}{P}}(OEthyl)_2$ |
| 4-Hydroxy-2,2,6,6-tetramethyl-1-oxylpiperidine | $HO-\overset{O}{\underset{\|}{P}}(Oiso\text{-Propyl})_2$ |
| 4-Hydroxy-2,2,6,6-tetramethyl-1-oxylpiperidine | $HO-\overset{O}{\underset{\|}{P}}(OPropyl)_2$ |
| 4-Hydroxy-2,2,6,6-tetramethyl-1-oxylpiperidine | $HO-\overset{O}{\underset{\|}{P}}(On\text{-Butyl})_2$ |
| 4-Hydroxy-2,2,6,6-tetramethyl-1-oxylpiperidine | $HO-\overset{O}{\underset{\|}{P}}(Osec\text{-Butyl})_2$ |
| 4-Hydroxy-2,2,6,6-tetramethyl-1-oxylpiperidine | $HO-\overset{O}{\underset{\|}{P}}(Otert.\text{-Butyl})_2$ |
| 4-Hydroxy-2,2,6,6-tetramethyl-1-oxylpiperidine | $HO-\overset{O}{\underset{\|}{P}}(OPhenyl)_2$ |
| 4-Hydroxy-2,2,6,6-tetramethyl-1-oxylpiperidine | $O=P(OH)_2(OMethyl)$ |
| 4-Hydroxy-2,2,6,6-tetramethyl-1-oxylpiperidine | $O=P(OH)_2(OEthyl)$ |
| 4-Hydroxy-2,2,6,6-tetramethyl-1-oxylpiperidine | $O=P(OH)_2(Oiso\text{-Propyl})$ |
| 4-Hydroxy-2,2,6,6-tetramethyl-1-oxylpiperidine | $O=P(OH)_2(OPropyl)$ |
| 4-Hydroxy-2,2,6,6-tetramethyl-1-oxylpiperidine | $O=P(OH)_2(On\text{-Butyl})$ |
| 4-Hydroxy-2,2,6,6-tetramethyl-1-oxylpiperidine | $O=P(OH)_2(Osec.\text{-Butyl})$ |
| 4-Hydroxy-2,2,6,6-tetramethyl-1-oxylpiperidine | $O=P(OH)_2(Otert.\text{-Butyl})$ |
| 4-Hydroxy-2,2,6,6-tetramethyl-1-oxylpiperidine | $O=P(OH)_2(OPhenyl)$ |
| 4-Methoxy-2,2,6,6-tetramethyl-1-oxylpiperidine | $P(OH)_3$ |
| 4-Methoxy-2,2,6,6-tetramethyl-1-oxylpiperidine | $P(OMethyl)_3$ |
| 4-Methoxy-2,2,6,6-tetramethyl-1-oxylpiperidine | $P(OEthyl)_3$ |
| 4-Methoxy-2,2,6,6-tetramethyl-1-oxylpiperidine | $P(Oiso\text{-Propyl})_3$ |
| 4-Methoxy-2,2,6,6-tetramethyl-1-oxylpiperidine | $P(OPropyl)_3$ |
| 4-Methoxy-2,2,6,6-tetramethyl-1-oxylpiperidine | $P(On\text{-Butyl})_3$ |
| 4-Methoxy-2,2,6,6-tetramethyl-1-oxylpiperidine | $P(Osec\text{-Butyl})_3$ |
| 4-Methoxy-2,2,6,6-tetramethyl-1-oxylpiperidine | $P(Otert.\text{-Butyl})_3$ |
| 4-Methoxy-2,2,6,6-tetramethyl-1-oxylpiperidine | $P(OPhenyl)_3$ |
| 4-Methoxy-2,2,6,6-tetramethyl-1-oxylpiperidine | $P(OH)(OMethyl)_2$ |
| 4-Methoxy-2,2,6,6-tetramethyl-1-oxylpiperidine | $P(OH)(OEthyl)_2$ |
| 4-Methoxy-2,2,6,6-tetramethyl-1-oxylpiperidine | $P(OH)(Oiso\text{-Propyl})_2$ |
| 4-Methoxy-2,2,6,6-tetramethyl-1-oxylpiperidine | $P(OH)(OPropyl)_2$ |
| 4-Methoxy-2,2,6,6-tetramethyl-1-oxylpiperidine | $P(OH)(On\text{-Butyl})_2$ |
| 4-Methoxy-2,2,6,6-tetramethyl-1-oxylpiperidine | $P(OH)(Osec\text{-Butyl})_2$ |
| 4-Methoxy-2,2,6,6-tetramethyl-1-oxylpiperidine | $P(OH)(Otert.\text{-Butyl})_2$ |
| 4-Methoxy-2,2,6,6-tetramethyl-1-oxylpiperidine | $P(OH)(OPhenyl)_2$ |
| 4-Methoxy-2,2,6,6-tetramethyl-1-oxylpiperidine | $P(OH)_2(OMethyl)$ |
| 4-Methoxy-2,2,6,6-tetramethyl-1-oxylpiperidine | $P(OH)_2(OEthyl)$ |
| 4-Methoxy-2,2,6,6-tetramethyl-1-oxylpiperidine | $P(OH)_2(Oiso\text{-Propyl})$ |
| 4-Methoxy-2,2,6,6-tetramethyl-1-oxylpiperidine | $P(OH)_2(OPropyl)$ |
| 4-Methoxy-2,2,6,6-tetramethyl-1-oxylpiperidine | $P(OH)_2(On\text{-Butyl})$ |
| 4-Methoxy-2,2,6,6-tetramethyl-1-oxylpiperidine | $P(OH)_2(Osec\text{-Butyl})$ |
| 4-Methoxy-2,2,6,6-tetramethyl-1-oxylpiperidine | $P(OH)_2(Otert.\text{-Butyl})$ |

| Inhibitor a) | Inhibitor b) |
|---|---|
| 4-Methoxy-2,2,6,6-tetramethyl-1-oxylpiperidine | P(OH)$_2$(OPhenyl) |
| 4-Methoxy-2,2,6,6-tetramethyl-1-oxylpiperidine | HP(OH)$_2$ |
| 4-Methoxy-2,2,6,6-tetramethyl-1-oxylpiperidine | (Methyl)P(OMethyl)$_2$ |
| 4-Methoxy-2,2,6,6-tetramethyl-1-oxylpiperidine | (Ethyl)P(OEthyl)$_2$ |
| 4-Methoxy-2,2,6,6-tetramethyl-1-oxylpiperidine | (iso-Propyl)P(Oiso-Propyl)$_2$ |
| 4-Methoxy-2,2,6,6-tetramethyl-1-oxylpiperidine | (Propyl)P(OPropyl)$_2$ |
| 4-Methoxy-2,2,6,6-tetramethyl-1-oxylpiperidine | (n-Butyl)P(On-Butyl)$_2$ |
| 4-Methoxy-2,2,6,6-tetramethyl-1-oxylpiperidine | (sec-Butyl)P(Osec-Butyl)$_2$ |
| 4-Methoxy-2,2,6,6-tetramethyl-1-oxylpiperidine | (tert.-Butyl)P(Otert.-Butyl)$_2$ |
| 4-Methoxy-2,2,6,6-tetramethyl-1-oxylpiperidine | (Phenyl)P(OPhenyl)$_2$ |
| 4-Methoxy-2,2,6,6-tetramethyl-1-oxylpiperidine | O=P(OH)$_3$ |
| 4-Methoxy-2,2,6,6-tetramethyl-1-oxylpiperidine | O=P(OMethyl)$_3$ |
| 4-Methoxy-2,2,6,6-tetramethyl-1-oxylpiperidine | O=P(OEthyl)$_3$ |
| 4-Methoxy-2,2,6,6-tetramethyl-1-oxylpiperidine | O=P(OPropyl)$_3$ |
| 4-Methoxy-2,2,6,6-tetramethyl-1-oxylpiperidine | O=P(Oiso-Propyl)$_3$ |
| 4-Methoxy-2,2,6,6-tetramethyl-1-oxylpiperidine | O=P(On-Butyl)$_3$ |
| 4-Methoxy-2,2,6,6-tetramethyl-1-oxylpiperidine | O=P(Osec-Butyl)$_3$ |
| 4-Methoxy-2,2,6,6-tetramethyl-1-oxylpiperidine | O=P(Otert.-Butyl)$_3$ |
| 4-Methoxy-2,2,6,6-tetramethyl-1-oxylpiperidine | O=P(OPhenyl)$_3$ |
| 4-Methoxy-2,2,6,6-tetramethyl-1-oxylpiperidine | HO—P(=O)(OMethyl)$_2$ |
| 4-Methoxy-2,2,6,6-tetramethyl-1-oxylpiperidine | HO—P(=O)(OEthyl)$_2$ |
| 4-Methoxy-2,2,6,6-tetramethyl-1-oxylpiperidine | HO—P(=O)(Oiso-Propyl)$_2$ |
| 4-Methoxy-2,2,6,6-tetramethyl-1-oxylpiperidine | HO—P(=O)(OPropyl)$_2$ |
| 4-Methoxy-2,2,6,6-tetramethyl-1-oxylpiperidine | HO—P(=O)(On-Butyl)$_2$ |
| 4-Methoxy-2,2,6,6-tetramethyl-1-oxylpiperidine | HO—P(=O)(Osec-Butyl)$_2$ |
| 4-Methoxy-2,2,6,6-tetramethyl-1-oxylpiperidine | HO—P(=O)(Otert.-Butyl)$_2$ |
| 4-Methoxy-2,2,6,6-tetramethyl-1-oxylpiperidine | HO—P(=O)(OPhenyl)$_2$ |
| 4-Methoxy-2,2,6,6-tetramethyl-1-oxylpiperidine | O=P(OH)$_2$(OMethyl) |
| 4-Methoxy-2,2,6,6-tetramethyl-1-oxylpiperidine | O=P(OH)$_2$(OEthyl) |
| 4-Methoxy-2,2,6,6-tetramethyl-1-oxylpiperidine | O=P(OH)$_2$(Oiso-Propyl) |
| 4-Methoxy-2,2,6,6-tetramethyl-1-oxylpiperidine | O=P(OH)$_2$(OPropyl) |
| 4-Methoxy-2,2,6,6-tetramethyl-1-oxylpiperidine | O=P(OH)$_2$(On-Butyl) |
| 4-Methoxy-2,2,6,6-tetramethyl-1-oxylpiperidine | O=P(OH)$_2$(Osec.-Butyl) |
| 4-Methoxy-2,2,6,6-tetramethyl-1-oxylpiperidine | O=P(OH)$_2$(Otert.-Butyl) |
| 4-Methoxy-2,2,6,6-tetramethyl-1-oxylpiperidine | O=P(OH)$_2$(OPhenyl) |
| 4-Oxo-2,2,6,6-tetramethyl-1-oxylpiperidine | P(OH)$_3$ |
| 4-Oxo-2,2,6,6-tetramethyl-1-oxylpiperidine | P(OMethyl)$_3$ |
| 4-Oxo-2,2,6,6-tetramethyl-1-oxylpiperidine | P(OEthyl)$_3$ |
| 4-Oxo-2,2,6,6-tetramethyl-1-oxylpiperidine | P(Oiso-Propyl)$_3$ |
| 4-Oxo-2,2,6,6-tetramethyl-1-oxylpiperidine | P(OPropyl)$_3$ |
| 4-Oxo-2,2,6,6-tetramethyl-1-oxylpiperidine | P(On-Butyl)$_3$ |
| 4-Oxo-2,2,6,6-tetramethyl-1-oxylpiperidine | P(Osec-Butyl)$_3$ |
| 4-Oxo-2,2,6,6-tetramethyl-1-oxylpiperidine | P(Otert.-Butyl)$_3$ |
| 4-Oxo-2,2,6,6-tetramethyl-1-oxylpiperidine | P(OPhenyl)$_3$ |
| 4-Oxo-2,2,6,6-tetramethyl-1-oxylpiperidine | P(OH)(OMethyl)$_2$ |
| 4-Oxo-2,2,6,6-tetramethyl-1-oxylpiperidine | P(OH)(OEthyl)$_2$ |
| 4-Oxo-2,2,6,6-tetramethyl-1-oxylpiperidine | P(OH)(Oiso-Propyl)$_2$ |
| 4-Oxo-2,2,6,6-tetramethyl-1-oxylpiperidine | P(OH)(OPropyl)$_2$ |
| 4-Oxo-2,2,6,6-tetramethyl-1-oxylpiperidine | P(OH)(On-Butyl)$_2$ |
| 4-Oxo-2,2,6,6-tetramethyl-1-oxylpiperidine | P(OH)(Osec-Butyl)$_2$ |
| 4-Oxo-2,2,6,6-tetramethyl-1-oxylpiperidine | P(OH)(Otert.-Butyl)$_2$ |
| 4-Oxo-2,2,6,6-tetramethyl-1-oxylpiperidine | P(OH)(OPhenyl)$_2$ |
| 4-Oxo-2,2,6,6-tetramethyl-1-oxylpiperidine | P(OH)$_2$(OMethyl) |
| 4-Oxo-2,2,6,6-tetramethyl-1-oxylpiperidine | P(OH)$_2$(OEthyl) |
| 4-Oxo-2,2,6,6-tetramethyl-1-oxylpiperidine | P(OH)$_2$(Oiso-Propyl) |
| 4-Oxo-2,2,6,6-tetramethyl-1-oxylpiperidine | P(OH)$_2$(OPropyl) |
| 4-Oxo-2,2,6,6-tetramethyl-1-oxylpiperidine | P(OH)$_2$(On-Butyl) |
| 4-Oxo-2,2,6,6-tetramethyl-1-oxylpiperidine | P(OH)$_2$(Osec-Butyl) |
| 4-Oxo-2,2,6,6-tetramethyl-1-oxylpiperidine | P(OH)$_2$(Otert.-Butyl) |
| 4-Oxo-2,2,6,6-tetramethyl-1-oxylpiperidine | P(OH)$_2$(OPhenyl) |
| 4-Oxo-2,2,6,6-tetramethyl-1-oxylpiperidine | HP(OH)$_2$ |
| 4-Oxo-2,2,6,6-tetramethyl-1-oxylpiperidine | (Methyl)P(OMethyl)$_2$ |
| 4-Oxo-2,2,6,6-tetramethyl-1-oxylpiperidine | (Ethyl)P(OEthyl)$_2$ |
| 4-Oxo-2,2,6,6-tetramethyl-1-oxylpiperidine | (iso-Propyl)P(Oiso-Propyl)$_2$ |
| 4-Oxo-2,2,6,6-tetramethyl-1-oxylpiperidine | (Propyl)P(OPropyl)$_2$ |
| 4-Oxo-2,2,6,6-tetramethyl-1-oxylpiperidine | (n-Butyl)P(On-Butyl)$_2$ |

| Inhibitor a) | Inhibitor b) |
|---|---|
| 4-Oxo-2,2,6,6-tetra-methyl-1-oxylpiperidine | (sec-Butyl)P(Osec-Butyl)$_2$ |
| 4-Oxo-2,2,6,6-tetra-methyl-1-oxylpiperidine | (tert.-Butyl)P(Otert.-Butyl)$_2$ |
| 4-Oxo-2,2,6,6-tetra-methyl-1-oxylpiperidine | (Phenyl)P(OPhenyl)$_2$ |
| 4-Oxo-2,2,6,6-tetra-methyl-1-oxylpiperidine | O=P(OH)$_3$ |
| 4-Oxo-2,2,6,6-tetra-methyl-1-oxylpiperidine | O=P(OMethyl)$_3$ |
| 4-Oxo-2,2,6,6-tetra-methyl-1-oxylpiperidine | O=P(OEthyl)$_3$ |
| 4-Oxo-2,2,6,6-tetra-methyl-1-oxylpiperidine | O=P(OPropyl)$_3$ |
| 4-Oxo-2,2,6,6-tetra-methyl-1-oxylpiperidine | O=P(Oiso-Propyl)$_3$ |
| 4-Oxo-2,2,6,6-tetra-methyl-1-oxylpiperidine | O=P(On-Butyl)$_3$ |
| 4-Oxo-2,2,6,6-tetra-methyl-1-oxylpiperidine | O=P(Osec-Butyl)$_3$ |
| 4-Oxo-2,2,6,6-tetra-methyl-1-oxylpiperidine | O=P(Otert.-Butyl)$_3$ |
| 4-Oxo-2,2,6,6-tetra-methyl-1-oxylpiperidine | O=P(OPhenyl)$_3$ |
| 4-Oxo-2,2,6,6-tetra-methyl-1-oxylpiperidine | HO—P(=O)(OMethyl)$_2$ |
| 4-Oxo-2,2,6,6-tetra-methyl-1-oxylpiperidine | HO—P(=O)(OEthyl)$_2$ |
| 4-Oxo-2,2,6,6-tetra-methyl-1-oxylpiperidine | HO—P(=O)(Oiso-Propyl)$_2$ |
| 4-Oxo-2,2,6,6-tetra-methyl-1-oxylpiperidine | HO—P(=O)(OPropyl)$_2$ |
| 4-Oxo-2,2,6,6-tetra-methyl-1-oxylpiperidine | HO—P(=O)(On-Butyl)$_2$ |
| 4-Oxo-2,2,6,6-tetra-methyl-1-oxylpiperidine | HO—P(=O)(Osec-Butyl)$_2$ |
| 4-Oxo-2,2,6,6-tetra-methyl-1-oxylpiperidine | HO—P(=O)(Otert.-Butyl)$_2$ |
| 4-Oxo-2,2,6,6-tetra-methyl-1-oxylpiperidine | HO—P(=O)(OPhenyl)$_2$ |
| 4-Oxo-2,2,6,6-tetra-methyl-1-oxylpiperidine | O=P(OH)$_2$(OMethyl) |
| 4-Oxo-2,2,6,6-tetra-methyl-1-oxylpiperidine | O=P(OH)$_2$(OEthyl) |
| 4-Oxo-2,2,6,6-tetra-methyl-1-oxylpiperidine | O=P(OH)$_2$(Oiso-Propyl) |
| 4-Oxo-2,2,6,6-tetra-methyl-1-oxylpiperidine | O=P(OH)$_2$(OPropyl) |
| 4-Oxo-2,2,6,6-tetra-methyl-1-oxylpiperidine | O=P(OH)$_2$(On-Butyl) |
| 4-Oxo-2,2,6,6-tetra-methyl-1-oxylpiperidine | O=P(OH)$_2$(Osec.-Butyl) |
| 4-Oxo-2,2,6,6-tetra-methyl-1-oxylpiperidine | O=P(OH)$_2$(Otert.-Butyl) |
| 4-Oxo-2,2,6,6-tetra-methyl-1-oxylpiperidine | O=P(OH)$_2$(OPhenyl) |
| N,N'-Bis(1-oxyl-2,2,6,6,-tetra-methylpiperidin-4-yl)-N,N'-bis-formyl-1,6-diaminohexane | P(OH)$_3$ |
| N,N'-Bis(1-Oxyl-2,2,6,6,-tetra-methylpiperidin-4-yl)-N,N'-bis-formyl-1,6-diaminohexane | P(OMethyl)$_3$ |
| N,N'-Bis(1-Oxyl-2,2,6,6,-tetra-methylpiperidin-4-yl)-N,N'-bis-formyl-1,6-diaminohexane | P(OEthyl)$_3$ |
| N,N'-Bis(1-Oxyl-2,2,6,6,-tetra-methylpiperidin-4-yl)-N,N'-bis-formyl-1,6-diaminohexane | P(Oiso-Propyl)$_3$ |
| N,N'-Bis(1-Oxyl-2,2,6,6,-tetra-methylpiperidin-4-yl)-N,N'-bis-formyl-1,6-diaminohexane | P(OPropyl)$_3$ |
| N,N'-Bis(1-Oxyl-2,2,6,6,-tetra-methylpiperidin-4-yl)-N,N'-bis-formyl-1,6-diaminohexane | P(On-Butyl)$_3$ |
| N,N'-Bis(1-Oxyl-2,2,6,6,-tetra-methylpiperidin-4-yl)-N,N'-bis-formyl-1,6-diaminohexane | P(Osec-Butyl)$_3$ |
| N,N'-Bis(1-Oxyl-2,2,6,6,-tetra-methylpiperidin-4-yl)-N,N'-bis-formyl-1,6-diaminohexane | P(Otert.-Butyl)$_3$ |
| N,N'-Bis(1-Oxyl-2,2,6,6,-tetra-methylpiperidin-4-yl)-N,N'-bis-formyl-1,6-diaminohexane | P(OPhenyl)$_3$ |
| N,N'-Bis(1-Oxyl-2,2,6,6,-tetra-methylpiperidin-4-yl)-N,N'-bis-formyl-1,6-diaminohexane | P(OH)(OMethyl)$_2$ |
| N,N'-Bis(1-Oxyl-2,2,6,6,-tetra-methylpiperidin-4-yl)-N,N'-bis-formyl-1,6-diaminohexane | P(OH)(OEthyl)$_2$ |
| N,N'-Bis(1-Oxyl-2,2,6,6,-tetra-methyl-1-oxylpiperidine formyl-1,6-diaminohexane | P(OH)(Oiso-Propyl)$_2$ |
| N,N'-Bis(1-Oxyl-2,2,6,6,-tetra-methylpiperidin-4-yl)-N,N'-bis-formyl-1,6-diaminohexane | P(OH)(OPropyl)$_2$ |
| N,N'-Bis(1-Oxyl-2,2,6,6,-tetra-methylpiperidin-4-yl)-N,N'-bis-formyl-1,6-diaminohexane | P(OH)(On-Butyl)$_2$ |
| N,N'-Bis(1-Oxyl-2,2,6,6,-tetra-methylpiperidin-4-yl)-N,N'-bis-formyl-1,6-diaminohexane | P(OH)(Osec-Butyl)$_2$ |
| N,N'-Bis(1-Oxyl-2,2,6,6,-tetra-methylpiperidin-4-yl)-N,N'-bis-formyl-1,6-diaminohexane | P(OH)(Otert.-Butyl)$_2$ |
| N,N'-Bis(1-Oxyl-2,2,6,6,-tetra-methylpiperidin-4-yl)-N,N'-bis-formyl-1,6-diaminohexane | P(OH)(OPhenyl)$_2$ |
| N,N'-Bis(1-Oxyl-2,2,6,6,-tetra-methylpiperidin-4-yl)-N,N'-bis-formyl-1,6-diaminohexane | P(OH)$_2$(OMethyl) |
| N,N'-Bis(1-Oxyl-2,2,6,6,-tetra-methylpiperidin-4-yl)-N,N'-bis-formyl-1,6-diaminohexane | P(OH)$_2$(OEthyl) |
| N,N'-Bis(1-Oxyl-2,2,6,6,-tetra-methylpiperidin-4-yl)-N,N'-bis-formyl-1,6-diaminohexane | P(OH)$_2$(Oiso-Propyl) |
| N,N'-Bis(1-Oxyl-2,2,6,6,-tetra-methylpiperidin-4-yl)-N,N'-bis-formyl-1,6-diaminohexane | P(OH)$_2$(OPropyl) |
| N,N'-Bis(1-Oxyl-2,2,6,6,-tetra-methylpiperidin-4-yl)-N,N'-bis-formyl-1,6-diaminohexane | P(OH)$_2$(On-Butyl) |
| N,N'-Bis(1-Oxyl-2,2,6,6,-tetra-methylpiperidin-4-yl)-N,N'-bis-formyl-1,6-diaminohexane | P(OH)$_2$(Osec-Butyl) |
| N,N'-Bis(1-Oxyl-2,2,6,6,-tetra-methylpiperidin-4-yl)-N,N'-bis-formyl-1,6-diaminohexane | P(OH)$_2$(Otert.-Butyl) |
| N,N'-Bis(1-Oxyl-2,2,6,6,-tetra-methylpiperidin-4-yl)-N,N'-bis-formyl-1,6-diaminohexane | P(OH)$_2$(OPhenyl) |

| Inhibitor a) | Inhibitor b) |
|---|---|
| N,N'-Bis(1-Oxyl-2,2,6,6,-tetra-methylpiperidin-4-yl)-N,N'-bis-formyl-1,6-diaminohexane | HP(OH)₂ |
| N,N'-Bis(1-Oxyl-2,2,6,6,-tetra-methylpiperidin-4-yl)-N,N'-bis-formyl-1,6-diaminohexane | (Methyl)P(OMethyl)₂ |
| N,N'-Bis(1-Oxyl-2,2,6,6,-tetra-methylpiperidin-4-yl)-N,N'-bis-formyl-1,6-diaminohexane | (Ethyl)P(OEthyl)₂ |
| N,N'-Bis(1-Oxyl-2,2,6,6,-tetra-methylpiperidin-4-yl)-N,N'-bis-formyl-1,6-diaminohexane | (iso-Propyl)P(Oiso-Propyl)₂ |
| N,N'-Bis(1-Oxyl-2,2,6,6,-tetra-methylpiperidin-4-yl)-N,N'-bis-formyl-1,6-diaminohexane | (Propyl)P(OPropyl)₂ |
| N,N'-Bis(1-Oxyl-2,2,6,6,-tetra-methylpiperidin-4-yl)-N,N'-bis-formyl-1,6-diaminohexane | (n-Butyl)P(On-Butyl)₂ |
| N,N'-Bis(1-Oxyl-2,2,6,6,-tetra-methylpiperidin-4-yl)-N,N'-bis-formyl-1,6-diaminohexane | (sec-Butyl)P(Osec-Butyl)₂ |
| N,N'-Bis(1-Oxyl-2,2,6,6,-tetra-methylpiperidin-4-yl)-N,N'-bis-formyl-1,6-diaminohexane | (tert.-Butyl)P(Otert.-Butyl)₂ |
| N,N'-Bis(1-Oxyl-2,2,6,6,-tetra-methylpiperidin-4-yl)-N,N'-bis-formyl-1,6-diaminohexane | (Phenyl)P(OPhenyl)₂ |
| N,N'-Bis(1-Oxyl-2,2,6,6,-tetra-methylpiperidin-4-yl)-N,N'-bis-formyl-1,6-diaminohexane | O=P(OH)₃ |
| N,N'-Bis(1-Oxyl-2,2,6,6,-tetra-methylpiperidin-4-yl)-N,N'-bis-formyl-1,6-diaminohexane | O=P(OMethyl)₃ |
| N,N'-Bis(1-Oxyl-2,2,6,6,-tetra-methylpiperidin-4-yl)-N,N'-bis-formyl-1,6-diaminohexane | O=P(OEthyl)₃ |
| N,N'-Bis(1-Oxyl-2,2,6,6,-tetra-methylpiperidin-4-yl)-N,N'-bis-formyl-1,6-diaminohexane | O=P(OPropyl)₃ |
| N,N'-Bis(1-Oxyl-2,2,6,6,-tetra-methylpiperidin-4-yl)-N,N'-bis-formyl-1,6-diaminohexane | O=P(Oiso-Propyl)₃ |
| N,N'-Bis(1-Oxyl-2,2,6,6,-tetra-methylpiperidin-4-yl)-N,N'-bis-formyl-1,6-diaminohexane | O=P(On-Butyl)₃ |
| N,N'-Bis(1-Oxyl-2,2,6,6,-tetra-methylpiperidin-4-yl)-N,N'-bis-formyl-1,6-diaminohexane | O=P(Osec-Butyl)₃ |
| N,N'-Bis(1-Oxyl-2,2,6,6,-tetra-methylpiperidin-4-yl)-N,N'-bis-formyl-1,6-diaminohexane | O=P(Otert.-Butyl)₃ |
| N,N'-Bis(1-Oxyl-2,2,6,6,-tetra-methylpiperidin-4-yl)-N,N'-bis-formyl-1,6-diaminohexane | O=P(OPhenyl)₃ |
| N,N'-Bis(1-Oxyl-2,2,6,6-tetra-methylpiperidin-4-yl)-N,N'-bis-formyl-1,6-diaminohexane | HO—P(=O)(OMethyl)₂ |
| N,N'-Bis(1-Oxyl-2,2,6,6-tetra-methylpiperidin-4-yl)-N,N'-bis-formyl-1,6-diaminohexane | HO—P(=O)(OEthyl)₂ |
| N,N'-Bis(1-Oxyl-2,2,6,6-tetra-methylpiperidin-4-yl)-N,N'-bis-formyl-1,6-diaminohexane | HO—P(=O)(Oiso-Propyl)₂ |
| N,N'-Bis(1-Oxyl-2,2,6,6-tetra-methylpiperidin-4-yl)-N,N'-bis-formyl-1,6-diaminohexane | HO—P(=O)(OPropyl)₂ |
| N,N'-Bis(1-Oxyl-2,2,6,6-tetra-methylpiperidin-4-yl)-N,N'-bis-formyl-1,6-diaminohexane | HO—P(=O)(On-Butyl)₂ |
| N,N'-Bis(1-Oxyl-2,2,6,6-tetra-methylpiperidin-4-yl)-N,N'-bis-formyl-1,6-diaminohexane | HO—P(=O)(Osec-Butyl)₂ |
| N,N'-Bis(1-Oxyl-2,2,6,6-tetra-methylpiperidin-4-yl)-N,N'-bis-formyl-1,6-diaminohexane | HO—P(=O)(Otert.-Butyl)₂ |
| N,N'-Bis(1-Oxyl-2,2,6,6-tetra-methylpiperidin-4-yl)-N,N'-bis-formyl-1,6-diaminohexane | HO—P(=O)(OPhenyl)₂ |
| N,N'-Bis(1-Oxyl-2,2,6,6,-tetra-methylpiperidin-4-yl)-N,N'-bis-formyl-1,6-diaminohexane | O=P(OH)₂(OMethyl) |
| N,N'-Bis(1-Oxyl-2,2,6,6,-tetra-methylpiperidin-4-yl)-N,N'-bis-formyl-1,6-diaminohexane | O=P(OH)₂(OEthyl) |
| N,N'-Bis(1-Oxyl-2,2,6,6,-tetra-methylpiperidin-4-yl)-N,N'-bis-formyl-1,6-diaminohexane | O=P(OH)₂(Oiso-Propyl) |
| N,N'-Bis(1-Oxyl-2,2,6,6,-tetra-methylpiperidin-4-yl)-N,N'-bis-formyl-1,6-diaminohexane | O=P(OH)₂(OPropyl) |
| N,N'-Bis(1-Oxyl-2,2,6,6,-tetra-methylpiperidin-4-yl)-N,N'-bis-formyl-1,6-diaminohexane | O=P(OH)₂(On-Butyl) |
| N,N'-Bis(1-Oxyl-2,2,6,6,-tetra-methylpiperidin-4-yl)-N,N'-bis-formyl-1,6-diaminohexane | O=P(OH)₂(Osec.-Butyl) |
| N,N'-Bis(1-Oxyl-2,2,6,6,-tetra-methylpiperidin-4-yl)-N,N'-bis-formyl-1,6-diaminohexane | O=P(OH)₂(Otert.-Butyl) |
| N,N'-Bis(1-Oxyl-2,2,6,6,-tetra-methylpiperidin-4-yl)-N,N'-bis-formyl-1,6-diaminohexane | O=P(OH)₂(OPhenyl) |
| Bis(1-Oxyl-2,2,6,6-tetra-methyl)piperidin-4-yl)sebacate | P(OH)₃ |
| Bis(1-Oxyl-2,2,6,6-tetra-methyl)piperidin-4-yl)sebacate | P(OMethyl)₃ |
| Bis(1-Oxyl-2,2,6,6-tetra-methyl)piperidin-4-yl)sebacate | P(OEthyl)₃ |
| Bis(1-Oxyl-2,2,6,6-tetra-methyl)piperidin-4-yl)sebacate | P(Oiso-Propyl)₃ |
| Bis(1-Oxyl-2,2,6,6-tetra-methyl)piperidin-4-yl)sebacate | P(OPropyl)₃ |
| Bis(1-Oxyl-2,2,6,6-tetra-methyl)piperidin-4-yl)sebacate | P(On-Butyl)₃ |
| Bis(1-Oxyl-2,2,6,6-tetra-methyl)piperidin-4-yl)sebacate | P(Osec-Butyl)₃ |
| Bis(1-Oxyl-2,2,6,6-tetra-methyl)piperidin-4-yl)sebacate | P(Otert.-Butyl)₃ |
| Bis(1-Oxyl-2,2,6,6-tetra-methyl)piperidin-4-yl)sebacate | P(OPhenyl)₃ |
| Bis(1-Oxyl-2,2,6,6-tetra-methyl)piperidin-4-yl)sebacate | P(OH)(OMethyl)₂ |
| Bis(1-Oxyl-2,2,6,6-tetra-methyl)piperidin-4-yl)sebacate | P(OH)(OEthyl)₂ |
| Bis(1-Oxyl-2,2,6,6-tetra-methyl)piperidin-4-yl)sebacate | P(OH)(Oiso-Propyl)₂ |
| Bis(1-Oxyl-2,2,6,6-tetra-methyl)piperidin-4-yl)sebacate | P(OH)(OPropyl)₂ |
| Bis(1-Oxyl-2,2,6,6-tetra-methyl)piperidin-4-yl)sebacate | P(OH)(On-Butyl)₂ |
| Bis(1-Oxyl-2,2,6,6-tetra-methyl)piperidin-4-yl)sebacate | P(OH)(Osec-Butyl)₂ |
| Bis(1-Oxyl-2,2,6,6-tetra-methyl)piperidin-4-yl)sebacate | P(OH)(Otert.-Butyl)₂ |
| Bis(1-Oxyl-2,2,6,6-tetra-methyl)piperidin-4-yl)sebacate | P(OH)(OPhenyl)₂ |
| Bis(1-Oxyl-2,2,6,6-tetra-methyl)piperidin-4-yl)sebacate | P(OH)₂(OMethyl) |
| Bis(1-Oxyl-2,2,6,6-tetra-methyl)piperidin-4-yl)sebacate | P(OH)₂(OEthyl) |
| Bis(1-Oxyl-2,2,6,6-tetra-methyl)piperidin-4-yl)sebacate | P(OH)₂(Oiso-Propyl) |

| Inhibitor a) | Inhibitor b) |
|---|---|
| Bis(1-Oxyl-2,2,6,6-tetra-methyl)piperidin-4-yl)sebacate | P(OH)$_2$(OPropyl) |
| Bis(1-Oxyl-2,2,6,6-tetra-methyl)piperidin-4-yl)sebacate | P(OH)$_2$(On-Butyl) |
| Bis(1-Oxyl-2,2,6,6-tetra-methyl)piperidin-4-yl)sebacate | P(OH)$_2$(Osec-Butyl) |
| Bis(1-Oxyl-2,2,6,6-tetra-methyl)piperidin-4-yl)sebacate | P(OH)$_2$(Otert.-Butyl) |
| Bis(1-Oxyl-2,2,6,6-tetra-methyl)piperidin-4-yl)sebacate | P(OH)$_2$(OPhenyl) |
| Bis(1-Oxyl-2,2,6,6-tetra-methyl)piperidin-4-yl)sebacate | HP(OH)$_2$ |
| Bis(1-Oxyl-2,2,6,6-tetra-methyl)piperidin-4-yl)sebacate | (Methyl)P(OMethyl)$_2$ |
| Bis(1-Oxyl-2,2,6,6-tetra-methyl)piperidin-4-yl)sebacate | (Ethyl)P(OEthyl)$_2$ |
| Bis(1-Oxyl-2,2,6,6-tetra-methyl)piperidin-4-yl)sebacate | (iso-Propyl)P(Oiso-Propyl)$_2$ |
| Bis(1-Oxyl-2,2,6,6-tetra-methyl)piperidin-4-yl)sebacate | (Propyl)P(OPropyl)$_2$ |
| Bis(1-Oxyl-2,2,6,6-tetra-methyl)piperidin-4-yl)sebacate | (n-Butyl)P(On-Butyl)$_2$ |
| Bis(1-Oxyl-2,2,6,6-tetra-methyl)piperidin-4-yl)sebacate | (sec-Butyl)P(Osec-Butyl)$_2$ |
| Bis(1-Oxyl-2,2,6,6-tetra-methyl)piperidin-4-yl)sebacate | (tert.-Butyl)P(Otert.-Butyl)$_2$ |
| Bis(1-Oxyl-2,2,6,6-tetra-methyl)piperidin-4-yl)sebacate | (Phenyl)P(OPhenyl)$_2$ |
| Bis(1-Oxyl-2,2,6,6-tetra-methyl)piperidin-4-yl)sebacate | O=P(OH)$_3$ |
| Bis(1-Oxyl-2,2,6,6-tetra-methyl)piperidin-4-yl)sebacate | O=P(OMethyl)$_3$ |
| Bis(1-Oxyl-2,2,6,6-tetra-methyl)piperidin-4-yl)sebacate | O=P(OEthyl)$_3$ |
| Bis(1-Oxyl-2,2,6,6-tetra-methyl)piperidin-4-yl)sebacate | O=P(OPropyl)$_3$ |
| Bis(1-Oxyl-2,2,6,6-tetra-methyl)piperidin-4-yl)sebacate | O=P(Oiso-Propyl)$_3$ |
| Bis(1-Oxyl-2,2,6,6-tetra-methyl)piperidin-4-yl)sebacate | O=P(On-Butyl)$_3$ |
| Bis(1-Oxyl-2,2,6,6-tetra-methyl)piperidin-4-yl)sebacate | O=P(Osec-Butyl)$_3$ |
| Bis(1-Oxyl-2,2,6,6-tetra-methyl)piperidin-4-yl)sebacate | O=P(Otert.-Butyl)$_3$ |
| Bis(1-Oxyl-2,2,6,6-tetra-methyl)piperidin-4-yl)sebacate | O=P(OPhenyl)$_3$ |
| Bis(1-Oxyl-2,2,6,6-tetra-methyl)piperidin-4-yl)sebacate | HO—P(=O)(OMethyl)$_2$ |
| Bis(1-Oxyl-2,2,6,6-tetra-methyl)piperidin-4-yl)sebacate | HO—P(=O)(OEthyl)$_2$ |
| Bis(1-Oxyl-2,2,6,6-tetra-methyl)piperidin-4-yl)sebacate | HO—P(=O)(Oiso-Propyl)$_2$ |
| Bis(1-Oxyl-2,2,6,6-tetra-methyl)piperidin-4-yl)sebacate | HO—P(=O)(OPropyl)$_2$ |
| Bis(1-Oxyl-2,2,6,6-tetra-methyl)piperidin-4-yl)sebacate | HO—P(=O)(On-Butyl)$_2$ |
| Bis(1-Oxyl-2,2,6,6-tetra-methyl)piperidin-4-yl)sebacate | HO—P(=O)(Osec-Butyl)$_2$ |
| Bis(1-Oxyl-2,2,6,6-tetra-methyl)piperidin-4-yl)sebacate | HO—P(=O)(Otert.-Butyl)$_2$ |
| Bis(1-Oxyl-2,2,6,6-tetra-methyl)piperidin-4-yl)sebacate | HO—P(=O)(OPhenyl)$_2$ |
| Bis(1-Oxyl-2,2,6,6-tetra-methyl)piperidin-4-yl)sebacate | O=P(OH)$_2$(OMethyl) |
| Bis(1-Oxyl-2,2,6,6-tetra-methyl)piperidin-4-yl)sebacate | O=P(OH)$_2$(OEthyl) |
| Bis(1-Oxyl-2,2,6,6-tetra-methyl)piperidin-4-yl)sebacate | O=P(OH)$_2$(Oiso-Propyl) |
| Bis(1-Oxyl-2,2,6,6-tetra-methyl)piperidin-4-yl)sebacate | O=P(OH)$_2$(OPropyl) |
| Bis(1-Oxyl-2,2,6,6-tetra-methyl)piperidin-4-yl)sebacate | O=P(OH)$_2$(On-Butyl) |
| Bis(1-Oxyl-2,2,6,6-tetra-methyl)piperidin-4-yl)sebacate | O=P(OH)$_2$(Osec.-Butyl) |
| Bis(1-Oxyl-2,2,6,6-tetra-methyl)piperidin-4-yl)sebacate | O=P(OH)$_2$(Otert.-Butyl) |
| Bis(1-Oxyl-2,2,6,6-tetra-methyl)piperidin-4-yl)sebacate | O=P(OH)$_2$(OPhenyl) |

They are particularly suitable for inhibiting the polymerization of (meth)acrolein, (meth)acrylic acid and esters thereof.

EXAMPLES AND COMPARATIVE EXAMPLES

General Experimental Conditions

Various polymerization inhibitors (in each case X ppm by weight, based on the amount of acrylic acid) were in each case added to 2 ml of acrylic acid and the mixture was enclosed gastight in a glass ampoule (20 ml inner volume) with air saturation.

The glass ampoule was then immersed in an oil bath at 125° C. so that the liquid level of the acrylic acid and the liquid level of the oil bath were at the same height. Thereafter, the time taken for the acrylic acid to undergo complete polymerization was determined (the visually determined time at which the acrylic acid had solidified).

The table below shows the results obtained.

| Example Ei and Comparative example Ci | Inhibitors | Time [min] |
|---|---|---|
| C 1 | 20 ppm by weight of 4-HO-TEMPO*) | 255 |
| C 2 | 20 ppm by weight of phenothiazine | 265 |
| E 1 | 100 ppm by weight of Irgafos 168, 20 ppm by weight of 4-HO-TEMPO | 390 |
| E 2 | 100 ppm by weight of Irgafos P-EPQ, 20 ppm by weight of 4-HO-TEMPO | 480 |
| E 3 | 100 ppm by weight of Ultranox 626, 20 ppm by weight of 4-HO-TEMPO | 490 |
| E 4 | 100 ppm by weight of H$_3$PO$_3$, 20 ppm by weight of 4-HO-TEMPO | 590 |
| C 3 | 100 ppm by weight of H$_3$PO$_3$ | 15 |
| C 4 | | 10 |
| C 5 | 100 ppm by weight of H$_3$PO$_4$ | 10 |
| E 5 | 20 ppm by weight of 4-HO-TEMPO 100 ppm by weight of phosphoric acid | 520 |
| E 6 | 20 ppm by weight of 4-HO-TEMPO 100 ppm by weight of dimethylphosphite | 525 |
| E 7 | 20 ppm by weight of 4-HO-TEMPO 100 ppm by weight of ammoniumhypophosphite | 520 |
| C 6 | 20 ppm by weight of BTEMPOD**) | 200 |
| E 8 | 20 ppm by weight of BTEMPOD 100 ppm by weight of Irgafos 168 | 330 |

-continued

| Example Ei and Comparative example Ci | Inhibitors | Time [min] |
|---|---|---|
| E 9 | 20 ppm by weight of BTEMPOD<br>100 ppm by weight of Ultranox 626 | 495 |
| E 10 | 20 ppm by weight of BTEMPOD<br>100 ppm by weight of $H_3PO_3$ | 660 |
| E 11 | 20 ppm by weight of BTEMPOD<br>100 ppm by weight of Irgafos P-EPQ | 665 |

*) 4-HO-TEMPO = 4-Hydroxy-2,2,6,6-tetramethyl-1-oxylpiperidine
**) N,N'-Bis(2,2,6,6-tetramethylpiperidin-1-oxyl-4-yl)-N,N'-bis-formyl-1,6-diaminohexane

We claim:

1. A process for stabilising chemical compounds which are present as pure substance or as a component of mixtures and have at least one ethylenically unsaturated group to undesired free radical polymerisation, in which polymerisation inhibitors which contain:
   a) at least one nitroxyl radical (inhibitors a)) and
   b) at least one chemical compound containing the element phosphorus in chemically bonded form (inhibitor b)) are added to the pure substance or the mixture, wherein the at least one inhibitor b) contains on the one hand no N-oxyl group and on the other hand at least a part of the phosphorus chemically bonded with an oxidation number ON of $-3 \leq ON \leq +5$, this phosphorus simultaneously being covalently bonded to at least one hetero atom different from carbon.

2. The process as claimed in claim 1, wherein the at least one inhibitor b) is orthophosphorous acid, a salt thereof and/or an ester thereof.

3. A process as claimed in claim 1, wherein the at least one nitroxyl radical is a piperidin and/or a pyrrolidin-N-oxyl radical.

4. A process as claimed in claim 1, wherein the at least one nitroxyl radical is 4-hydroxy-2,2,6,6-tetramethyl-1-oxylpiperidine.

5. A process as claimed in claim 1, wherein the chemical compound having at least one ethylenically unsaturated group is at least one monomer from the group consisting of acrylic acid, methacrylic acid, acrolein, methacrolein, acrylates and methacrylates.

6. A mixture containing at least one nitroxyl radical (inhibitors a)) and at least one chemical compound containing the element phosphorus in chemically bonded form (inhibitors b)), with the proviso that the at least one inhibitor b) contains on the one hand no N-oxyl group and on the other hand at least a part of the phosphorus chemically bonded with an oxidation number ON of $-3 \leq ON \leq +5$, this phosphorus simultaneously being covalently bonded to at least one hetero atom differing from carbon.

7. A mixture as claimed in claim 6, in which the at least one inhibitor b) is orthophosphorous acid, a salt thereof and/or an ester thereof.

8. A mixture as claimed in claim 6, in which the at least one nitroxyl radical is a piperidin- and/or a pyrrolidin-N-oxyl radical.

9. A mixture as claimed in claim 6, in which the at least one nitroxyl radical is 4-hydroxy-2,2,6,6-tetramethyl-1-oxylpiperidine.

10. The use of a mixture as claimed in claim 6 as a polymerisation inhibitor for compounds which are present as pure substance or as a component of mixtures and have at least one ethylenically unsaturated group.

11. A mixture containing at least one compound having at least one ethylenically unsaturated group, at least one nitroxyl radical (inhibitors a)) and at least one chemical compound containing the element phosphorus in chemically bonded form (inhibitors b)), with the proviso that the at least one inhibitor b) contains on the one hand no N-oxyl group and on the other hand at least a part of the phosphorus chemically bonded with the oxidation number ON of $-3 \leq ON \leq +5$, this phosphorus simultaneously being covalently bonded to at least one hetero atom differing from carbon.

* * * * *